Figure 1:
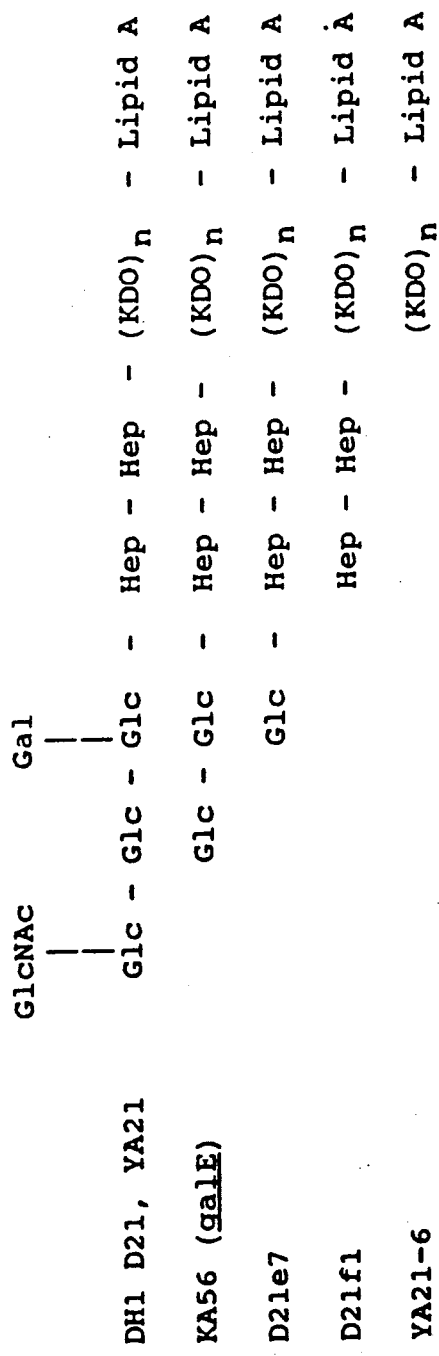
Figure 1:
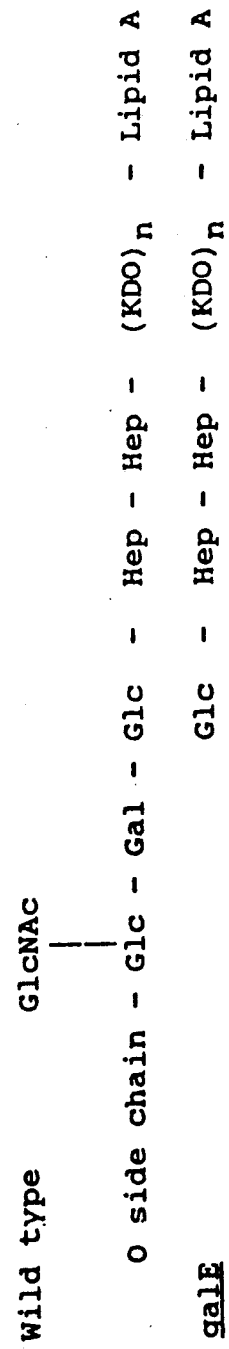

United States Patent [19]

Morona et al.

[11] Patent Number: 5,110,588
[45] Date of Patent: May 5, 1992

[54] COMPOSITE SALMONELLA E. COLI, VIBRIO CHOLERAE VACCINE STRAINS

[75] Inventors: Renato Morona, Aberfoyle Park; Stephen R. Attridge, Salisbury Park, both of Australia

[73] Assignee: Enterovax Limited, Salisbury South, Australia

[21] Appl. No.: 401,403

[22] Filed: Sep. 1, 1989

Related U.S. Application Data

[63] Continuation-in-part of Ser. No. 86,354, Aug. 17, 1987, abandoned.

[30] Foreign Application Priority Data

Aug. 19, 1986 [AU] Australia .................. PH7545
Sep. 1, 1988 [AU] Australia .................. PJ0186
Nov. 2, 1988 [AU] Australia .................. PJ1273

[51] Int. Cl.⁵ .................. A61K 39/116; A61K 39/106; A61K 39/108; A61K 39/112
[52] U.S. Cl. .................. 424/92; 435/172.2; 435/172.3; 435/252.3; 435/252.33; 935/65
[58] Field of Search .................. 424/93, 92; 435/172.2, 435/172.3, 252.3, 252.33, 252.8, 909, 849, 879; 935/65

[56] References Cited

U.S. PATENT DOCUMENTS 4,588,170 12/1989 Curtis. III .................. 424/93
4,632,830 12/1986 Formal et al. .................. 424/92

OTHER PUBLICATIONS

Rick, P. D., 1987 "Lipopolysaccharide Biosynthesis", In *Escherichia coli and Salmonella Typhimurium*, Ed. Neidhardt, F. C. American Society for Microbiology, Washington, DC pp. 648–662.

Raetz, C. R. V. 1987, "Structure and Biosynthesis of Lipid A in *Escherichia coli*" In *Escherichia coli and Salmonella Typhimurium*, Ed. Neidhardt, F. C. American Society for Microbiology, Washington DC, pp. 498–503.

Godard, C., et al. Biological Abstracts vol. 64, No. 9, p. 4917, Abstract 50115.

Guinee, P. A. M. et al. 1989, Biological Abstracts, vol. 87 No. 9, Abstract 93143.

Baron, L. S. et al. 1987, Infection and Immunity, vol. 55, No. 11, pp. 2797–2801.

Hohmann, A., et al. 1979, Infection and Immunity, vol. 25, No. 1, pp. 27–33.

Schmidt, et al.; Immunochemistry of R Lipopolysaccharides of *E. coli*; Eur. J. Biochem 16:382–392 (1970).

Primary Examiner—Richard A. Schwartz
Assistant Examiner—Mary E. Mosher
Attorney, Agent, or Firm—Iver P. Cooper

[57] ABSTRACT

Composite bacterial strains useful as vaccines for the prophylactic treatment of enteric diseases are hybrids of Salmonella and *E. coli* in which *E. coli*-derived lipopolysaccharide cores expressed in a Salmonella organism serve as a scaffold upon which the O-antigen of yet another pathogenic bacterial species, such as *Vibrio cholerae* is constructed. Such strains, methods of their production, vaccine compositions comprising these strains, and methods of treating enteric disease with these vaccine compositions, are disclosed.

16 Claims, 22 Drawing Sheets

A B C D E F G H J K L

A B C D E

A B C

A B C

A B C D E F

COMPOSITE SALMONELLA E. COLI, VIBRIO CHOLERAE VACCINE STRAINS

This application is a continuation-in-part of U.S. Ser. No. 07/086,354, filed Aug. 17, 1987, now abandoned.

BACKGROUND OF THE INVENTION

The present invention relates to hybrid bacterial trains which may be used for the expression of high levels of *Vibrio cholerae O-somatic antigen (Vc OAg).*

The genes encoding the O-antigen from both serotypes of *Vibrio cholerae* have been cloned into *E.coli* K-12. Such plasmid clones are pPM1001, pPM1002, pPM1003, and pPM1004 which is derived from pPM1001. [These plasmids have been described in a previous patent application PCT/AU85/00015, now allowed U.S. Ser. No. 07/080,362, the entire disclosure of which is incorporated herein by reference, and in Manning et al, (1986) Infect. Immun 53(2) 272-277]. E.coli K-12 strains harbouring these plasmids produce high levels of Vc OAg which is in the form of a lipopolysaccharide (LPS) since it is extractable by the standard hot phenol/water method, is detectable by silver staining of cell envelope material electrophoresed on a SDS-polyactylamide gel, and it is on the cell surface of clones as judged by agglutination with antiserum to *Vibrio cholerae.*

However, when pPM1004 is introduced into either *Salmonella typhimurium* strain G30, or into *Salmonella typhi* strain Ty21a, both galE mutant strains, the Vc OAg is produced at low levels and is not in the form of a lipopolysaccharide since it cannot be extracted by the hot phenol/water method and cannot be silver stained as described above. Since these, and other Salmonella strains, express the Vc OAg poorly, then this is a major obstacle to the use of Salmonellae as a carrier strain for Vc OAg in a live oral vaccine; Vc OAg is known to be a protective antigen for immunity to cholera.

Poor expression of Vc OAg in Salmonella relative to the expression obtained in *E.coli* K-12 may be the result of any one of the many differences between the two species. The block (or blocks) in expression may occur at the level of gene expression or biosynthesis and assembly.

It is accordingly an object of the present invention to overcome, or at least alleviate one or more of the difficulties related to the prior art.

SUMMARY OF THE INVENTION

In accordance therewith one major difference between *E.coli* and *Salmonella* which has now been investigated and which is thought to be significant resides in the difference in the composition of the core region of the LPS between the two species. FIG. 1 shows the arrangement and composition of the core sugars in the LPS on *E.coli* K-12 and *Salmonella typhimurium.* It is interesting to note that a galE mutant of *E.coli* K-12 would have a glucose-glucose terminus in its LPS, whereas a *Salmonella galE* mutant would have a monoglucose residue as the terminal sugar.

The role of the LPS core in the Vc OAg expression in *E.coli* K-12 was investigated by examining the expression of Vc OAg (Ogawa type) in various *E.coli* K-12 strains which have defects affecting the LPS core. In summary, *E.coli* K-12 strains with a wild type or galE-type LPS core expressed Vc OAg. No expression of Vc OAg was observed in *E.coli* K-12 mutant strains which lack heptose and glucose or glucose only, or have only one glucose residue in the LPS core, (FIG. 1). This result indicates that in *E.coli* K-12 the Vc OAg is assembled onto the *E.coli* K-12 LPS core. Furthermore, the most likely requirement in terms of core sugars is that a terminal di-glucose must be present since "galE" type LPS is an efficient acceptor of Vc OAg chains (FIG. 1).

The Salmonella LPS core has no terminal di-glucose because of the position of the galactose residue, and a *Salmonella galE* mutant produces LPS with a single terminal glucose (FIG. 1).

These observations support our hypothesis that the Salmonella LPS core is not a suitable acceptor for Vc OAg.

Accordingly, in a first aspect, the present invention provides an avirulent strain of Salmonella including a fragment of DNA containing genes encoding the synthesis of at least a portion of the core region of an *E.coli* strain.

The *E.coli* strain may be an *E.coli* K-12 strain. The locus included in the fragment of DNA is referred to as *rFa.* Thus, to circumvent the problem of the prior art, *Salmonella-E.coli* K-12 hybrid strains were constructed by transferring to Salmonella the region of the *E.coli* K-12 chromosome which encodes the enzymes required to make the core region of the LPS. This locus, rfa, is located at about 81 min. on the *E.coli* K-12 genetic map.

Such *Salmonella-E.coli* hybrid strains, with *rfa* from *E.coli* K-12 [$(rfa)^{K-12}$], when constructed to harbour the appropriate plasmid clone, may express Vc OAg at high levels in the form of a lipopolysaccharide, and furthermore can also produce Salmonella O-somatic antigen in the form of a lipopolysaccharide.

In order to construct the *Salmonella-E.coli* hybrid strains described above, in a further aspect the present invention provides an strain modified to encode specific antibiotic resistance, which is located in the bacterial chromosome near and which is an Hfr strain transferring both rfa and the antibiotic-resistance marker early.

The *E.coli* strain may be an *E.coli* K-12 strain. The *E.coli* K-12 strain may be of any suitable type. It will be understood that the modification to encode for specific antibiotic resistance makes it possible to select exconjugants, using such strains as donors, in which the rfa region has been transferred, at high probability, to the recipients.

For example, the *E.coli* Hfr strains may encode resistance to chloramphenicol. The *E.coli* K-12 strain may be modified to include an mtl::Tn9 insertion mutation (Mtl maps near rfa). The modification may be undertaken by transduction.

The Salmonella strain may be a *Salmonella typhimurium* or *Salmonella typhi* strain. The *Salmonella* strain may be selected from *Salmonella typhimurium* strain LB5010, *Salmonella typhimurium* LT2 *rfaG, Salmonella typhimurium* G30, *Salmonella typhi* V487, variants thereof and mutants thereof.

In the description following reference will be made to a number of *Escherichia coli, Salmonella typhimurium* and *Salmonella typhi* strains by their codes. Each of these strains is maintained in the culture collection of the University of Adelaide, Australia. Table 1 attached sets out the codes and the relevant characteristics of each of the bacterial strains referred to below.

Examples of the *E.coli* K-12 donor strains for use in the preparation of the hybrid strains described above are those designated EX170, EX173, and EX260, samples of which are maintained in the culture collection of the University of Adelaide, Australia. Accordingly, in a further preferred aspect of the present invention there is provided *E.coli* donor strains EX170, EX173, and EX260; variants thereof and mutants thereof.

The rfa locus of *E.coli* K-12 maps at about 81 min on the genetic map, very close to the genes for mannitol utilization, mtl. The (rfa)$^{K-12}$ region was introduced into Salmonella by means of Hfr mediated chromosomal gene transfer. The Hfr strain PK3 was used: the origin of transfer is at about 78 min, and transfer of (rfa)$^{K-12}$ as an early marker occurs in an anti-clockwise direction. In order to be able to select for the transfer of E.coli genes, strain PK3 was modified by transduction to have a mtl::Tn9 insertion mutation [Tn9 encodes resistance to chloramphenicol]. The mtl locus is located between the Hfr transfer origin and (rfa)$^{K-12}$, and the chloramphenicol resistance determinant allows direct selection for transfer of the E.coli chromosome. Since mtl and (rfa)$^{K-12}$ are closely linked, it was expected that the majority of recipients receiving mtl::Tn9 would also receive (rfa)$^{K-12}$.

The donor strain constructed was called EX170. It can be contraselected with an antibiotic to which the recipient is resistant. This donor also has several growth factor requirements (threonine and leucine requirement) which can also be used to contraselect the donor.

Alternatively, or in addition, an E.coli donor strain may be modified to encode specific sensitivity to sodium deoxycholate. The E.coli may be modified to include a tolC210::Tn10 insertion mutation. The mutation may be inserted utilising a transduction.

For example, another donor strain, called EX260, is described. It is derived from EX170 and differs from it in that it has a tolC210::Tn10 insertion mutation. This additional mutation allows the donor to be contraselected by using 0.02% w/v sodium deoxycholate in the selection media. This would allow selection for transfer of (rfa)$^{K-12}$ on nutrient medium since both chloramphenicol and deoxycholate are all that is needed to select Salmonella-*E.coli* hybrids.

Other Hfr donor strains may be constructed utilising similar techniques. Utilising a similar process to that used to construct EX170, the *E.coli* strain KL228 which transfers the rfa region early in a clockwise direction (from an origin at about 84 min) was made mtl::Tn9 by transduction. This resulting strain was called EX173.

The donor strains so formed may be utilised in the preparation of *Salmonella-E.coli* hybrids as described above. Thus, in a still further aspect of the present invention there is provided a method of preparing an avirulent Salmonella strain including a fragment of DNA containing genes encoding the synthesis of at least a portion of the core region of an E.coli strain which method includes
providing
(i) an avirulent strain of Salmonella, and
(ii) an E.coli Hfr strain modified to encode a specific antibiotic resistance marker which is located in the bacterial chromosome near the locus, rfa transferring both rfa and the antibiotic-resistance marker;
permitting the strains to conjugate; and
selecting composite products so formed utilising the specific antibiotic resistance encoded in the *E.coli* strain and a counterselection for the donor.

The conjugation may be a Hfr mediated chromosomal gene transfer.

The E.coli strain may be selected from the donor strains described above.

In a preferred form, the avirulent strain of Salmonella may include a defined non-revertible mutation in the galE gene. The galE mutation may thus be a marker for the *Salmonella-E.coli* hybrids formed.

The avirulent Salmonella strains may be *Salmonella typhi* strains, *Salmonella typhimurium* strains or other strains of Salmonella.

In a preferred form, the avirulent strain of Salmonella may further include
a fragment of DNA containing genes encoding the synthesis of an O-antigen.

The O-antigen may be the *Vibrio cholerae* O-antigen (Vc OAg).

The avirulent strain of Salmonella may be modified to include the genes expressing the O-antigen via transformation with a suitable plasmid.

Thus, in a preferred aspect, the method of preparing an avirulent Salmonella strain as described above may further include providing a plasmid containing genes encoding the expression of an O-antigen and bearing a $thyA^+$ non-antibiotic marker, and a thyA derivative of the avirulent Salmonella strain described above; and inserting the cloned genes on the plasmid into the avirulent thyA Salmonella strain by transformation.

Techniques for preparing plasmids bearing thyA non-antibiotic markers are described in our co-pending Australian Patent Application 74202/87 the entire disclosure of which is incorporated herein by reference. Plasmids pEVX8 and pEVX9 described therein as expressing the O-antigen and having $thyA^+$ as a positive selection marker may be used.

Accordingly in a further preferred aspect of the present invention, there is provided an avirulent *Salmonella - E.coli* composite strain including a *thyA* avirulent strain of *Salmonella typhi;* a first fragment of DNA containing genes including the locus, *rfa,* located at approximately 81 min on the *E.coli* K-12 genetic map and including the enzymes required to form the core region of the lipopolysaccharide; and a second fragment of DNA containing genes encoding the expression of an O-antigen and bearing a $thyA^+$ non-antibiotic marker; the said first and second fragments of DNA being inserted into the avirulent thyA Salmonella typhi strain.

Examples of avirulent *Salmonella-E.coli* hybrid strains of the type described above are those designated EX200, EX225, EX262, EX206, EX210, EX363, EX645 and EX880 described below. Strains EX206, EX210, EX363, EX645 and EX880 also carry a plasmid expressing Vc OAg. Samples of each of these strains are maintained in the culture collection of the University of Adelaide, Australia.

Accordingly, in a preferred aspect of the present invention, there is provided the avirulent *Salmonella-E.coli* hybrid strains listed above, and in Table 1.

According to a still further aspect of the present invention, there is provided a vaccine composition useful for effecting immunity against enteric diseases including an avirulent *Salmonella - E.coli* composite strain including a thyA avirulent strain of Salmonella typhi:

a first fragment of DNA containing genes including the locus, rfa. located at approximately 81 min on the E.coli K-12 genetic map and including the enzymes required to form the core region of the lipopolysaccharide; and a second fragment of DNA containing genes encoding the expression of an O-antigen and bearing a thyA+ non-antibiotic marker; the said first and second fragments of DNA being inserted into the avirulent thyA Salmonella typhi strain.

The enteric disease may be cholera. The O-antigen may be *Vibrio cholerae* O-somatic antigen (Vc OAg).

The avirulent strain may be selected from EX206, EX210, EX363, EX645 and EX880 derivatives thereof and mutants thereof.

In a further aspect of the present invention, there is provided a method for the prophylactic treatment of enteric diseases in mammals which method includes administering to the mammal a prophylactically effective amount of the vaccine composition described above.

The invention will now be more fully described with reference to the accompanying examples. It should be understood, however, that the description following is illustrative only and should not be taken in any way as a restriction on the generality of the invention described above.

EXAMPLE 1:

CONSTRUCTION OF STRAINS OF SALMONELLA WITH RFA$^{K-12}$

Construction of Strain EX200

Strain EX170 was mated with the Salmonella typhimurium strain LB5010. Exconjugants which were str$^R$ (streptomycin resistant), ilv+ met+ (growth without isoleucine and valine, and methionine), and chloramphenicol

BRIEF DESCRIPTION OF THE DRAWINGS

FIG. 1 Structure of *E. coli* K-12 and Salmonella LPS.

FIG. 2 Derivation of strains of interest.

FIG. 3 SDS-PAGE (with LPS-specific silver straining) of material from various stains. Bacteria were grown in nutrient broth with glucose (0.5% w/v) and proteinase K-treated material (from about $10^8$ bacteria/-track) was subjected to SDS-PAGE with IPS-specific silver staining. A: KL96, B: V484, C: *V. cholerae* 569B. The *V. cholerae* LPS region is arrowed.

FIG. 4 Construction of pPM1004. Plasmid pPM1001 was cut with NaeI, and ligated with SmaI-cut pSC101 to give pPM1004. Dark segment: pHC79 DNA; light segment: DNA from *V. cholerae;* hatched segment: pSC101 DNA.

FIG. 5 SDS-PAGE (with LPS-specific silver staining) of LPS from strains of interest. Bacteria were grown in nutrient broth with no sugar supplementation (-), with glucose (0.5% w/v) (G) or with both glucose and galactose (0.2% w/v) (GG). Proteinase K-treated material (from about $10^8$ bacteria/track) was subjected to SDS-PAGE with LPS-specific silver straining. A: Ty21a (G) B: Ty21a (GG) C: V487 (G) D: V487 (GG) E: EX210 (-) F: EX210 (GG) G: EX256 (G) H: EX256 (GG) J: EX645 (-) K: EX645 (GG) L: *V cholerae* 569B. Glucose was omitted from the stains in track E and J because the sugar, when present in the nutrient broth (but no minimal medium), inhibits the production of *V. cholerae*-like LPS strains harboring pEVX22. The single arrow indicates *V. cholerae*-like LPS, the double arrow *S. typhi* LPS. The boxed area is a staining artifact.

FIG. 6 SDS-PAGE (with LPS-specific silver staining) of the LPS core regions of strains of interest. Bacteria were grown in nutrient broth with glucose (0.5% w/v) and galactose (0.2% w/v). Proteinase K-treated material (from about $10^8$ bacteria/track) was subjected to SDS-PAGE followed by LPS-specific silver staining. Only the core region of the gel is shown. A: KL96, B: EX170, C: Ty21a, D: EX256, E: EX645. The open arrow indicates the core (the lowest band) of strains carrying the rfa genes of *E. coli* K-12. The closed arrow indicates the core (the lowest band) of Ty21a. The bracket indicates the region of the gel showing material consisting of one to several O-antigen units attached to core.

FIG. 7 construction of pEVX5. The details are given below. Light segment: pSC101 DNA excluding the Tc$^R$ gene; dark segment: Tc$^R$ gene of pSC101; hatched segment: thyA+ gene from pBTAH.

FIG. 8 Construction of pOmpV500. The details are given below. Light segment: pBR322 DNA excluding Ap$^R$ or Tc$^R$ genes; dark segment: Ap$^R$ or Tc$^R$ genes of pBR322; hatched segment: OmpV gene.

FIG. 9 Construction of pEVX20 and pEVX22. The details are given below. Light segment: V. cholerae DNA capable, in E. coli K-12, of encoding genes required for synthesis of V. cholerae o-antigen (Inaba); dotted segment: pompV500 DNA excluding Tc$^R$ or ompV genes; vertically hatched segment: Tc$^R$ gene of pOmpV500; diagonally hatched segment: ompV gene of pompV500; cross hatched segment: pEVX5 excluding thyA gene; dark segment: thyA gene of pEVX5.

FIG. 10 SDS-PAGE with protein-specific staining of cell membrane preparations from 2 strains. Bacteria were grown in nutrient broth and cell membrane material (from about $10^8$ bacteria/track) subjected to SDS-PAGE followed by protein-specific staining. A: Ty21a, B: EX645, C: Protein molecular weight markers. The arrows indicate markers of (from top to bottom) 94, 67, 43, 30, 20.1 and 14.4 kilodaltons, respectively.

FIG. 11 [$^{14}$C]-galactose labels the Salmonella-type LPS of EX645. Ty21a or EX645 were pulse-labelled with [$^{14}$C]-galactose, and proteinase K-treated cells run on SDS-PAGE, followed by autoradiography. Tracks A: Ty21a; Tracks B: EX645. The high molecular weight LPS characteristic of Salmonella is arrowed. Alternate tracks are empty.

FIG. 12 Immunoblot (using anti-*V. cholerae* antiserum) of LPS of strains of interest. Bacteria were grown in nutrient broth with no sugar supplement (-), with glucose (0.5% w/v) (G) or with glucose and galactose (0.2% w/v) (GG). Proteinase K-treated material (from about $10^8$ bacteria/track) were subjected to SDS-PAGE followed by transfer to nitrocellulose and immunoblotting with an anti-V. cholerae antiserum. A: EX645 (-), B: EX645 (GG), C: V. cholerae 569B (G). The arrow indicates V. cholerae-like LPS.

FIG. 13 Immunogold electron microscopy of strains of interest. Bacteria, grown in minimal medium with or without galactose were subjected to immunogold electron microscopy with antisera as shown below.

| Panel | Magnification ($\times 10^{-3}$) | Galactose added to growth medium | Strain | Antiserum |
|---|---|---|---|---|
| A | 30 | No | *V. cholerae* | anti-C |

-continued

| Panel | Magnification ($\times 10^{-3}$) | Galactose added to growth medium | Strain | Antiserum |
|---|---|---|---|---|
| B | 30 | No | 569B V. cholerae 569B | anti-Ty2Vi$^-$ |
| C | 20 | No | EX256 | anti-C |
| D | 20 | No | EX256 | anti-Ty2Vi$^-$ |
| E | 20 | No | EX645 | anti-C |
| F | 20 | No | EX645 | anti-Ty2Vi$^-$ |
| G | 20 | Yes | EX645 | anti-C |
| H | 20 | Yes | EX645 | anti-Ty2Vi$^-$ |

Anti-C antiserum is a monoclonal anti-[V. cholerae LPS C antigen].
Anti-Ty2Vi$^-$ antiserum was raised against a via derivative of S. typhi Ty2, and is largely anti-[O-antigen of S. typhi].

Figure 14A:
Figure 14B:

FIG. 14 individual EX645 bacteria express both S. typhi LPS and V. cholerae-like LPS. The LPS types expressed by EX645 were examined by immunogold electron microscopy. Bacteria were grown in minimal medium with galactose (as for panels G and H of FIG. 12), and, after labelling, examined at low magnification (6000x). Typical fields are shown. Examination of 200 bacteria showed that essentially 100% of the bacteria expressed V. cholerae-like LPS. These results were consistent with the results of differential plate counting. FIG. 14(a) shows screening with polyclonal anti-[S. typhi]-serum and 14(b), with anti-[V. cholerae LPS]-antibody (mouse monoclonal anti-C).

Figure 15:
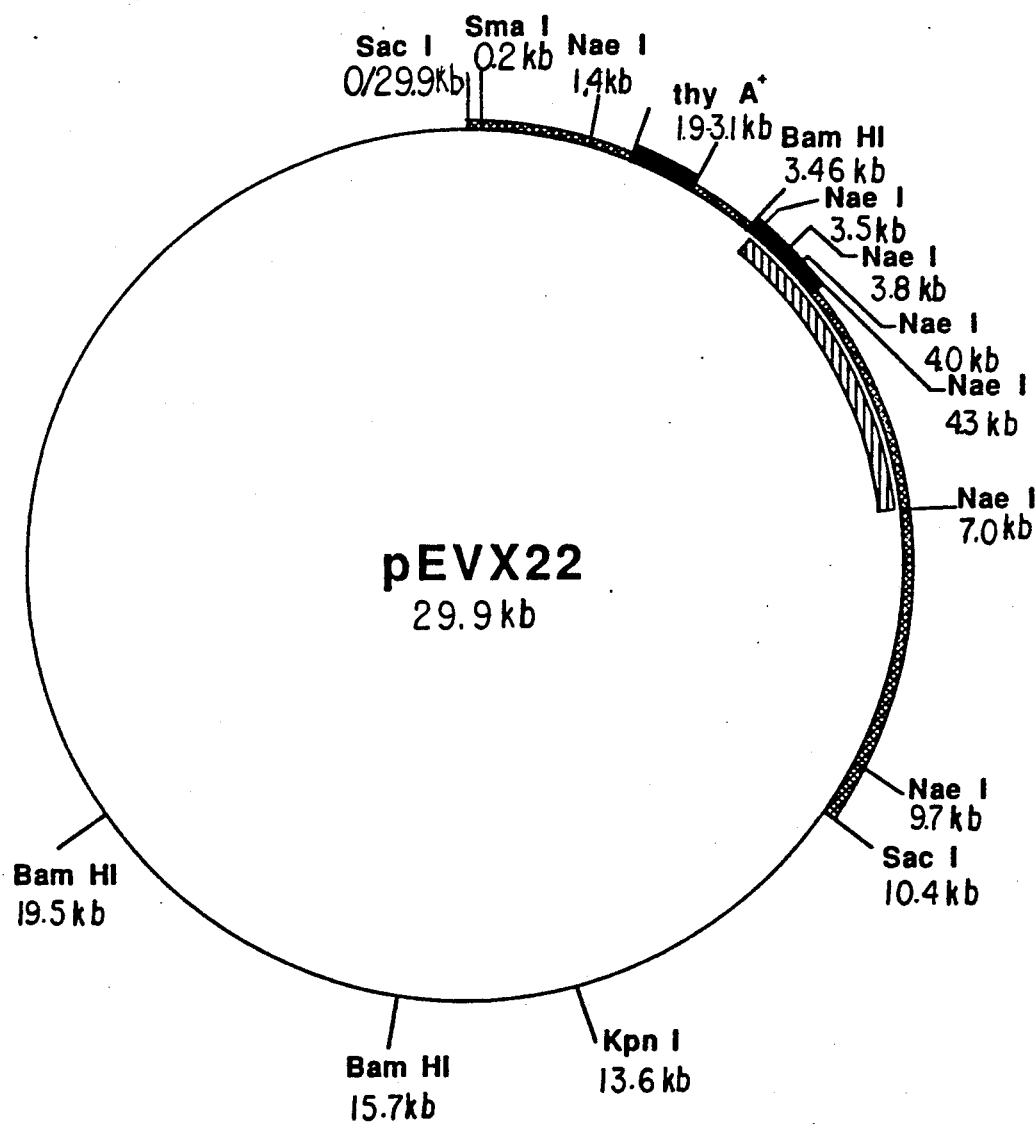

FIG. 15 Plasmid pEVX22 - Restriction Enzyme Sites. Sites of various restriction enzymes were mapped on pEVX22. cross hatched segment: plasmid pEVX5, horizontally hatched segment: thyA gene, dark segment: Tc$^R$ gene of pSC101, vertically hatched segment: site of NaeI deletion to produce pEXV59, single line: V. cholerae Inaba DNA.

Figure 16:
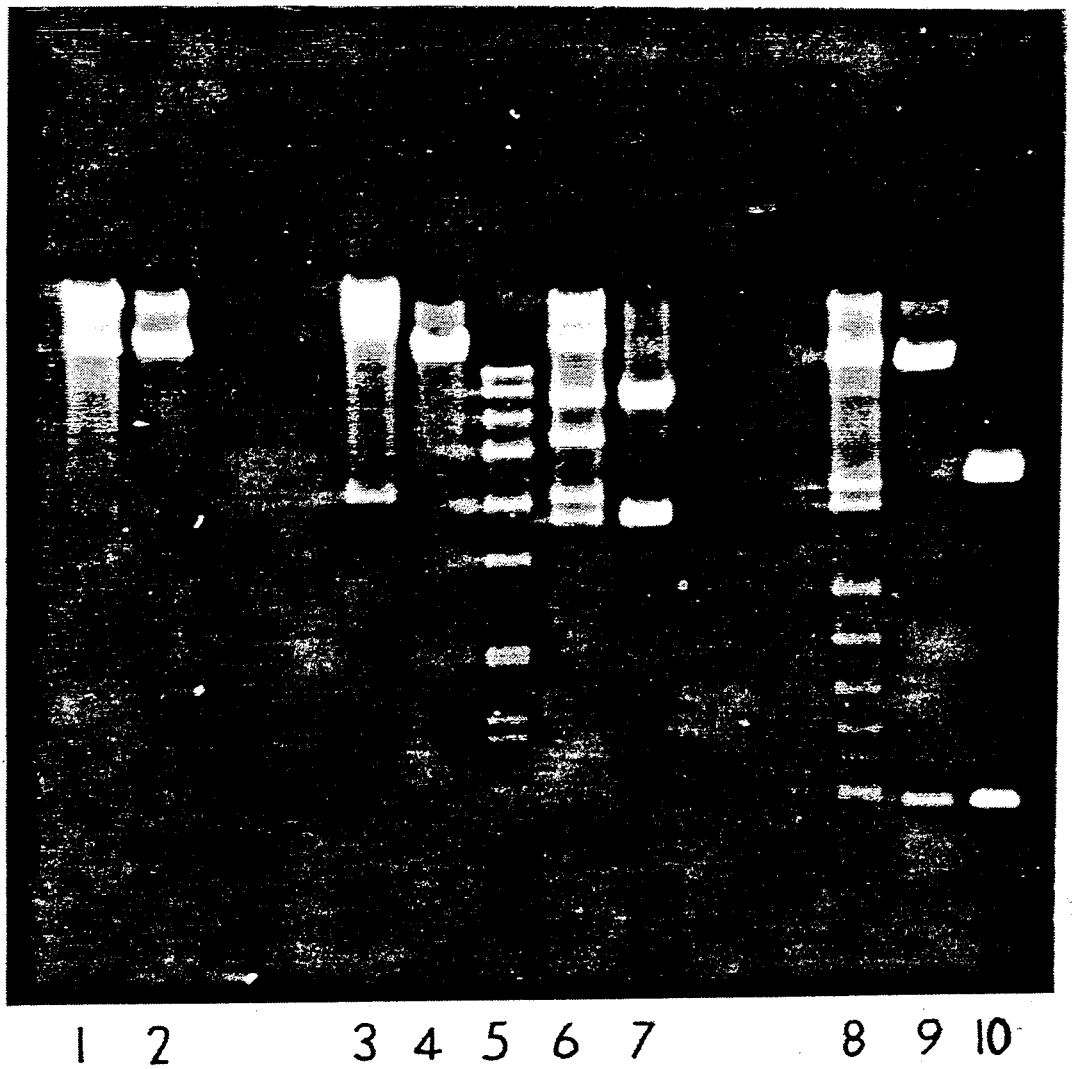

FIG. 16 Restriction enzyme digests of pEVX22, pEVX5 and pBTAH. 1. pEVX22 (SacI); 2. pEVX5 (SacI); 3. pEVX22 (BamHI); 4. pEVX5 (BamHI); 5. Phage SPP1 (EcoRI) (molecular size markers of 8.0, 7.1, 6.0, 4.78, 3.44, 2.77, 1.93, 1.88, 1.55, 1.45, 1.2, 1.03 and 0.7 kilobase); 6. pEVX22 (BamHI and SacI); 7. pEVX5 (BamHI and SacI); 8. pEVX22 (HindIII); 9. pEVX5 (HindIII); 10. PBTAH (HindIII).

Figure 17:
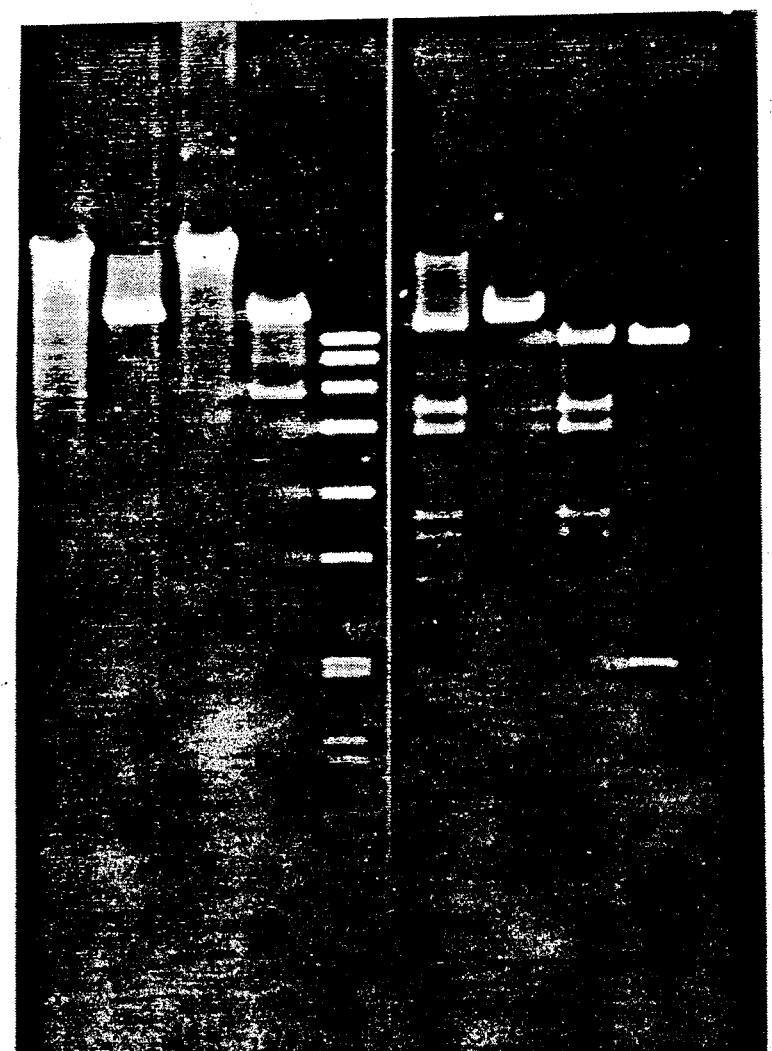

FIG. 17 Restriction enzyme digests of pEVX22 and pEVX5. 1 pEVX22 (SmaI); 2. pEVX5 (SmaI); 3. pEVX22 (HpaI); 4. pEVX5 (HpaI); 5. Phage SPP1 (EcoRI) (molecular size markers of 8.0, 7.1, 6.0, 4.78, 3.44, 2.77, 1.93, 1.88, 1.55, 1.45, 1.2, 1.03 and 0.7 kilobases); 6. pEVX22 (EcoRI); 7. pEVX5 (EcoRI); 8. pEVX22 (EcoRI and SacI); 9. pEVX5 (EcoRI and SacI).

Figure 18:
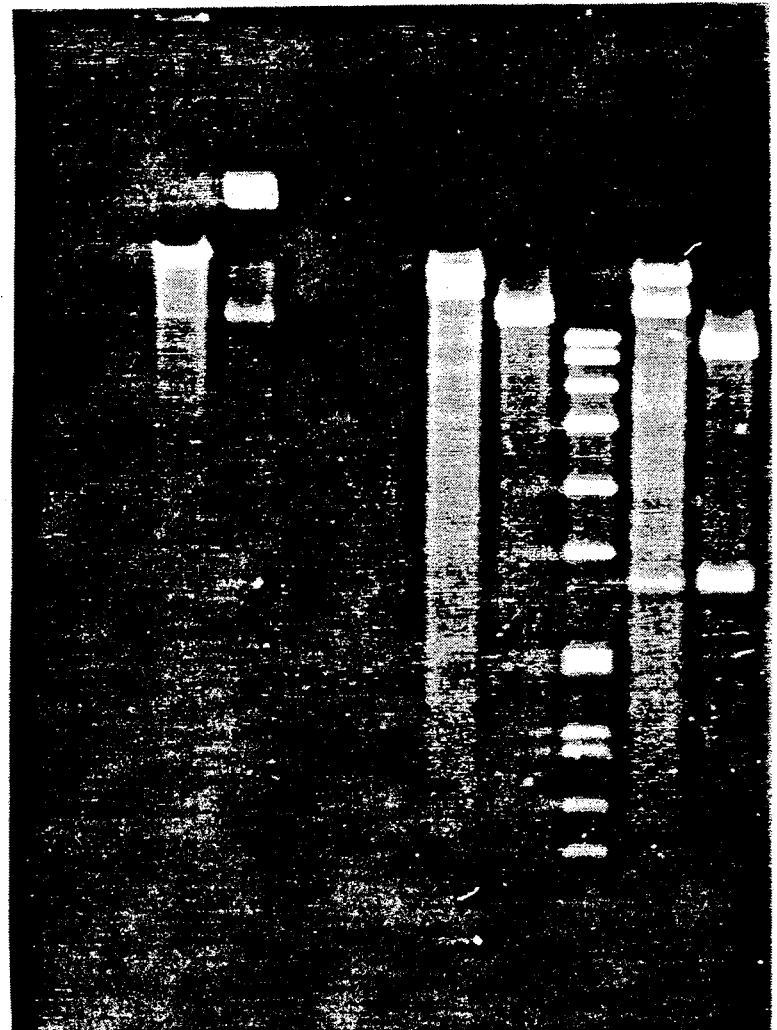

FIG. 18 Restriction enzyme digests of pEVX22 and pEVX5. 1. pEVX22 (KpnI); 2. pEVX5 (KpnI); 3. pEVX22 (SmaI and KpnI); 4. pEVX5 (SmaI and KpnI); 5. Phage SPP1 (EcoRI) Molecular size markers of 8.0, 7.1, 6.0, 4.78, 3.44, 2.77, 1.93, 1.88, 1.55, 1.45, 1.2, 1.03 and 0.7 kilobases); 6. pEVX22 (SmaI and PstI); 7. pEVX5 (SmaI and PstI).

Figure 19:
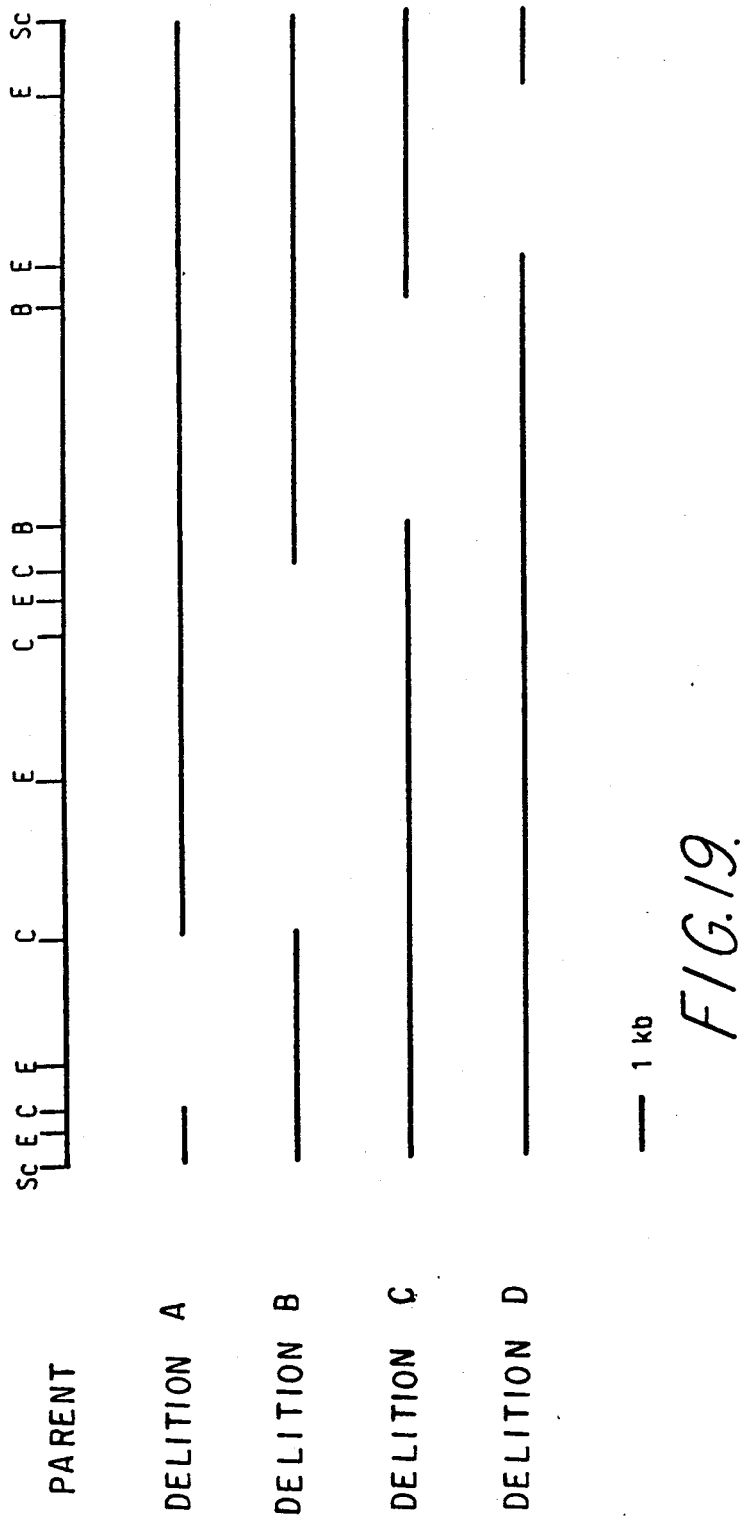
Figure 20:
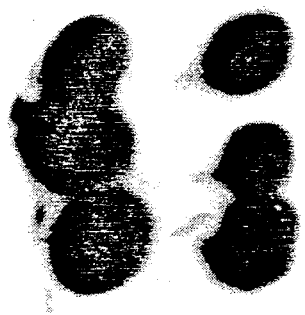
Figure 20:

FIG. 19 Deletion mutagenesis of the 20 kb SacI fragment encoding the biosynthesis of O-antigen characteristics of V. cholerae 017. The 20kb SacI fragment of pEVX7 was subjected to deletion mutagenesis (partial restriction enzyme digestion, followed by re-ligation) and truncated plasmids screened for their ability to produce V. cholerae-like O-antigen in E. coli K-12. Some results are shown. Sc: SacI site; E: EcoRI site; C: ClaI site; B: BamHI site.

FIG. 20 EX645 does not possess DNA homologous to the LT-B fragment of *E. coli* enterotoxin. Strains 569B (A), EX645 (B), *E. coli* 071 (LT+) (C), DH1 (D), Ty21A (E) and EX256 (F) were patched onto a nitrocellulose filter resting on a plate of minimal medium agar, and grew for 40h at 37° C. The bacteria were lysed in situ and probed with either [$^{32}$P]-LT-B probe (a 0.75 kb HindIII fragment covering the LT-B and part of the LT-A gene, from pEDW299 or [=P]-pADE107, a 7.5kb plasmid carrying the *Salmonella typhimurium gal* operon). Top panel: LT-B probing; Bottom panel: gal probing.

FIG. 21 Plasmid pEVX59 - Restriction Enzyme Sites. Sites of various restriction enzymes were mapped on pEVX59. cross hatched segment: plasmid pEVX5; diagonally hatched segment: thyA gene; dark segment: remaining Tc$^R$ gene of pSC101 after digestion of NaeI; single line: *V. cholerae* Inaba DNA.

DETAILED DESCRIPTION OF THE PREFERRED EMBODIMENTS

EXAMPLE 1

CONSTRUCTION OF STRAINS OF SALMONELLA WITH RFA$^{K\text{-}12}$

Construction of Strain EX200

Strain EX170 was mated with the Salmonella typhimurium strain LB5010. Exconjugants which were str$^R$ (streptomycin resistant), ilv+ met+ (growth without isoleucine and valine, and methionine), and chloramphenicol resistant (mtl::Tn9) were selected.

Such *Salmonella-E.coli* hybrids were expected to have *E.coli* K-12 chromosome between 80 min and 88 min, replacing the equivalent region of the Salmonella chromosome. Such exconjugants must have the (rfa)$^{K\text{-}12}$ locus. Since strain LB5010 is also a galE mutant, the effect on the LPS of *Salmonella typhimurium* could be determined by testing with LPS-dependent bacteriophages. Phage P22 requires O-antigen as its receptor, phage Felix O (FO) requires intact core, and phages P1 and C21 require a core with terminal glucose.

Salmonella-E.coli hybrids of the desired phenotype were found among the exconjugants. One such hybrid, called EX200 was found to be resistant to phage FO when tested on media containing galactose. FO is a phage which uses intact Salmonella LPS core region to adsorb and does not infect E.coli K-12. Hence the Salmonella rfa locus most likely has been replaced by the *E.coli* K-12 rfa locus. Since EX200 is sensitive to phage P22 when the growth media contains galactose, this demonstrates that the *Salmonella typhimurium* O-antigen is assembled onto the E.coli K-12 LPS core sugars. These observations are supported by the data obtained with *Salmonella typhi* (see below).

To test if a Salmonella strain with (rfa)$^{K\text{-}12}$ could express the Vc OAg, plasmids pEVX8 and pEVX9 [these plasmids are described in Australian patent application number 76269/87] were transformed into a thyA derivative of EX200, called EX361. Such transformants expressed the Vc OAg as judged by slide agglutination with an anti-*Vibrio cholerae* serum.

In another experiment, plasmid pPM1004 was introduced into EX200 by mating with EX178. One exconjugant strain EX216, produced Vc OAg comparable to *E.coli* K-12 strains having pPM1004, as judged by silver staining of cell envelopes electrophoresed on an SDS-polyacrylamide gel.

Construction of strain EX225

Strain EX170 was mated with SGSC262, a *Salmonella typhimurium* LT2 *rfaG* mutant, and $cml^R$ (chloramphenicol resistant), $str^R$ exconjugants were selected. All exconjugants tested become rfaG+, namely they become sensitive to the O-antigen specific phage P22, and resistant to the core-specific phage P1 and C21. Hence the rfa region of *E.coli* K-12 can be efficiently transferred to *Salmonella*, confirming the results above. An example of such an exconjugant is EX225. This strain and all other exconjugants obtained were ilv+ (located at 84 min.), indicating that this marker is closely linked to mtl and rfa.

Other exconjugants also became xyl+ (located at 79 min.), but none were met+ (located at 89 min.). Hence the amount of *E.coli* chromosome received from the donor is at most limited to a few minutes on either side of the mtl marker.

Construction of strain EX262

A derivative of Salmonella typhimurium G-30 which had the $(rfa)^{K-12}$ region was constructed as follows.

The generalised transducing phage P1vir was grown on strain EX200. This phage lysate was used to infect G30 and chloramphenicol-resistant transductant colonies were selected. One transductant was recovered, and called EX262.

The strain was resistant to phage FO on nutrient medium with galactose. Most transductants were mtl+ suggesting that the transposon Tn9 had moved to another location during the transduction event.

Strain EX262 behaved identically to G30 in terms of its ability to colonize Peyer's patches in mice. This indicated that the $(rfa)^{K-12}$ did not influence this characteristic of *Salmonella typhimurium*. It should be noted that few transductants were obtained in this cross. This is most likely due to a low recombination frequency between the *E.coli* K-12 chromosomal DNA on either side of $(mtl::Tn9)^{K-12}$ in strain EX200, and the analogous region in G30.

EXAMPLE 2

CONSTRUCTION OF A SALMONELLA TYPHIMURIUM STRAIN WITH RFA$^{K-12}$ AND Vc OAg

Construction of strain EX206

Strain V490 is *Salmonella typhimurium* G30 but $str^R$ and carrying pPM1004 ($tet^R$, (tetracycline resistant), Vc OAg clone). This strain expresses Vc OAg poorly. Strain EX173 was mated with V490 and $cml^R$, $str^R$, $tet^R$ (pPM1004 retention), exconjugants were selected.

Among the exconjugants, which were screened for Vc OAg production by SDS-PAGE and silver staining, one was found which expressed high levels of Vc OAg. This strain was called EX206.

Strain EX206 was found to be mtl+ (i.e. mannitol fermentation positive), yet was $cml^R$. This strain may have Tn9 relocated to another place in the chromosome (see above). The alternative possibility is that an F' mtl::Tn9 was transferred during the mating. However, examination of the plasmid content of EX206 did not reveal the presence of an F' but it did show pPM1004 and the Salmonella typhimurium cryptic plasmid.

EXAMPLE 3

CONSTRUCTION OF A SALMONELLA TYPHI Ty21a STRAIN WITH RFAK-12 AND Vc OAg

Construction of strain EX210

Strain V487, which is Ty21a but $rif^R$ (rifampicin resistant), and which harbours pPM1004 ($tet^R$, Vc OAg clone), was mated with strain EX170 and $cml^R$ $rif^R$ $tet^R$ exconjugants were selected on the appropriately supplemented nutrient media. The resulting colonies were examined for Vc OAg expression by silver staining of cell envelope material separated on an SDS-polyacrylamide gel. The presence of LPS molecules with the *E.coli* K-12 core instead of Salmonella core in the hybrid strains could be detected by silver staining of cell envelopes or whole cell lysates separated by SDS-PAGE. One exconjugant which expressed Vc OAg and was mtl− was called EX210.

Strain EX210 was resistant to phage FO even when galactose was added to media, but sensitive to phage P22 indicating that the Salmonella O-antigen is expressed in this strain. This strain produces Vc OAg as LPS since it is extractable by the hot phenol/water method. Vc OAg is detectable by silver staining of cell envelopes, or whole cell lysates separated by SDS-PAGE. When galactose is added to the media, both Salmonella O-antigen and Vc OAg can be detected by silver staining. EX210 cells can be agglutinated by antiserum to *Vibrio cholerae* showing that the OAg is on the cell surface. Isolated LPS from EX210 inhibits specifically in a haemagglutination inhibition assay, using sheep red blood cells (SRBC) coated with *Vibrio cholerae* 569B LPS. Formalin fixed EX210 cells also inhibit in such an assay. These assays suggest that EX210 produces 10%-50% w/w of the Vc OAg produced by *Vibrio cholerae* itself.

LPS isolated from EX210, EX210 killed by formalin, and live EX210 itself can elicit an immune response to 569B LPS in rabbits.

Strain EX210 is a potential live oral vaccine for cholera.

Construction of Strain EX363

Strain EX363 was constructed by methods similar to those used in the construction of EX645, which are described in the next section.

Strain EX210 was cured of PPM1004 by spontaneous loss to give EX233. A spontaneous mtl+ revertant of EX233 was selected on minimal media and was called strain EX256. A thyA mutant of EX256 was selected by plating on minimal media with thymine and trimethoprim. This strain was called EX259 and was found to be non-reverting ($<1$ in $10^8$). Hence EX259 is Ty21a $rif^R$ $(rfa)^{K\text{-}12}$ thyA. The thyA+ Vc OAg (Ogawa type) plasmid pEVX14 was transferred to strain EX259 by mating strain EX259 with strain EX320. Selection was for thu+ (deoxycholate resistant) exconjugants. The resulting colonies were screened for plasmid content. One exconjugant was found which had pEVX14, and was called strain EX363. This strain expressed Vc OAg as judged by silver staining of whole cell lysates treated with proteinase K and electrophoresed on an SDS-polyacrylamide gel.

EX363 is a potential live oral vaccine for cholera, and has only one antibiotic resistant marker, $rif^R$.

The Salmonella $(rfa)^{K\text{-}12}$ hybrid strains may be useful for the expression of O-antigens from other gram-negative pathogens, if such O-antigens are protective antigens: an example of this may be the O-antigen of Shigella species. Further modification of the Salmonella strains may be required if expression is not achieved. For example, expression may require (rfa)$^{K-12}$ and another chromosomal region of *E.coli* K-12.

Apart from the *E.coli* K-12 LPS core sugar structure at least four other types are known. Such core types may be required for the expression of various types of O-antigen. Hence a series of Salmonella strains could be constructed with each of the LPS core types. These would be useful for the expression of O-antigens from different gram-negative pathogens.

EXAMPLE 4

CONSTRUCTION OF A SALMONELLA TYPHI Ty21a STRAIN WITH RFAK-12AND Vc OAg (INABA) (EX645)

EX645 is based on the attenuated *S.typhi* strain Ty21a, which has had extensive field-testing as a typhoid vaccine, and which has been shown to be safe and effective in this role. The strain Ty21a has been shown to be safe when given orally to man in doses of up to $10^{11}$ organisms. Strain EX645 differs from Ty21a in four respects:

(a) The strain carries a spontaneous mutation to rifampicin-resistance (rpoB).
(b) The strain carries a non-reverting thyA$^-$ mutation.
(c) The strain has received (in the mtl-rfa region, min. 78-81) an amount (possibly up to 200 kb) of DNA from *Escherichia coli* K-12, including the E.coli K-12 rfa genes. This DNA has replaced the S.typhi DNA in this region.
(d) The strain carries a plasmid of 30.4 kb, which is composed of the pSC101 vector (9.3 kb) but with the tetracycline-resistance gene inactivated by insertion at the HindIII site of a 1.12 kb fragment from *E.coli* K-12 carrying the thyA$^+$ gene, and with a 20 kb SacI fragment from *V.cholerae* 569B (Classical, Inaba) sufficient, in *E.coli* K-12, to encode the synthesis of O-antigen apparently very similar to that made by *V.cholerae* 569B.

STRAIN CONSTRUCTION

1. The carrier strain (modified Ty21a)

This section contains the modifications made to Ty21a in order to make it a suitable carrier for the recombinant plasmid carrying the V.cholerae O-antigen genes (rfb genes).

1.1 Rationale for modifying S.typhi Ty21a

The carrier is different from Ty21a in 3 chromosomal locations.

(a) Rifampin-resistance: The rifampicin-resistance property of the strain is designed to allow its easy and efficient detection. Rifampin-resistance is used because the rpoB mutation arises spontaneously in Salmonella at a frequency of 1 in $10^6$, is stable once selected, and because rifampicin is not an antibiotic of choice in the treatment of gastrointestinal or systemic infections.

(b) thyA$^-$ mutation: In the construction of a strain which carries a recombinant plasmid, it is necessary to be able to select for carrier bacteria which receive the plasmid in an efficient plasmid introduction process, which may be transformation or conjugation [conjugation with a donor carrying a "non-mobilisable" plasmid with a replicon such as that of pSC101 results in very low plasmid transfer]. Normally, the recombinant plasmid would carry an antibiotic-resistance marker, and selection of the required strain would then depend on the mediation by such a strain of resistance to the antibiotic in question. It is not appropriate that a strain designed for administration to man should be resistant to antibiotics commonly used in man such as tetracycline or ampicillin. We have devised a selection system for plasmid transfer which is not based upon such a property. In this system, the recombinant plasmid carries a functional thyA+ gene (encoding the enzyme thymidylate synthetase, which is required for the biosynthesis of an essential component, thymine). The carrier strain carries a non-reverting mutation (thyA$^-$) to thymine-dependence. Hence, introduction of the plasmid will complement thymine auxotrophy and the required recombinant strain may be selected on thymine-free media. Bacteria which lose the plasmid in vivo will become thyA$^-$ and hence resistant to trimethoprim. This, in itself, is not considered to create a problem since trimethoprim is not the treatment of choice against enteric infections. Transfer of the thyA$^-$ mutation to other organisms is discussed later but could not be detected at levels as low as 1 in $10^9$.

(c) rfa region modification: Early in our studies we obtained recombinant plasmids carrying DNA from *V.cholerae* which, in *E.coli* K-12, were sufficient to give rise to a material identifiable by sodium dodecyl sulfate-polyacrylamide gel electrophoresis (SDS-PAGE) as LPS similar to that of *V.cholerae* (data below). When such plasmids were transferred to Salmonella strains, including Ty21a, no such material was evident. It was hypothesised that the *V.cholerae* O-antigenic material could not polymerise on the Salmonella LPS core. Hence, the rfa (core-biosynthetic) region of *E.coli* K-12 was transferred to Salmonella strains by an Hfr cross. Such exconjugants were now capable of the synthesis of recognisable (SDS-PAGE) *V.cholerae*-like LPS. In summary, the vaccine strain has a replacement of Ty21a DNA by *E.coli* K-12 DNA in the *mtl* region because the critical *V.cholerae* antigen is not well expressed in a strain background with *rfa* of *Salmonella,* but is well expressed when *rfa* genes derived from *E.coli* K-12 are present in the strain.

The amount of DNA replaced in this modification is likely to be small as *E.coli* and *Salmonella* DNA have low homology and integration of donor DNA occurs about $10^7$-fold less frequently than in intraspecific crosses. We have not attempted to define the amount of DNA transferred, but it is important to note that the strain EX645 still resembles Ty21a in a range of specific characteristics and in its behaviour when taken orally by human volunteers. It is reasonable to assume that only one fragment of DNA was incorporated. One crossover point must lie between the point of origin, lying between xyl (about 79.7) and malA (75). The other end must lie beyond rfa at 81.2 : recombination between Salmonella and *E.coli* is reported to occur primarily at highly conserved genes such as rrn. There are rrn gene clusters at 82 min. and 85 min. in *S.typhimurium* and presumably also in *S. typhi,* as they are in general conserved between *S.typhimurium* LT2 and *E.coli* K-12. Therefore, one end could be expected to have been between 75 and 79.7 and the other at about 82 or 85, if recombination took place at one of the rrn gene clusters.

1.2 The carrier strain modifications in detail

Figure 2:
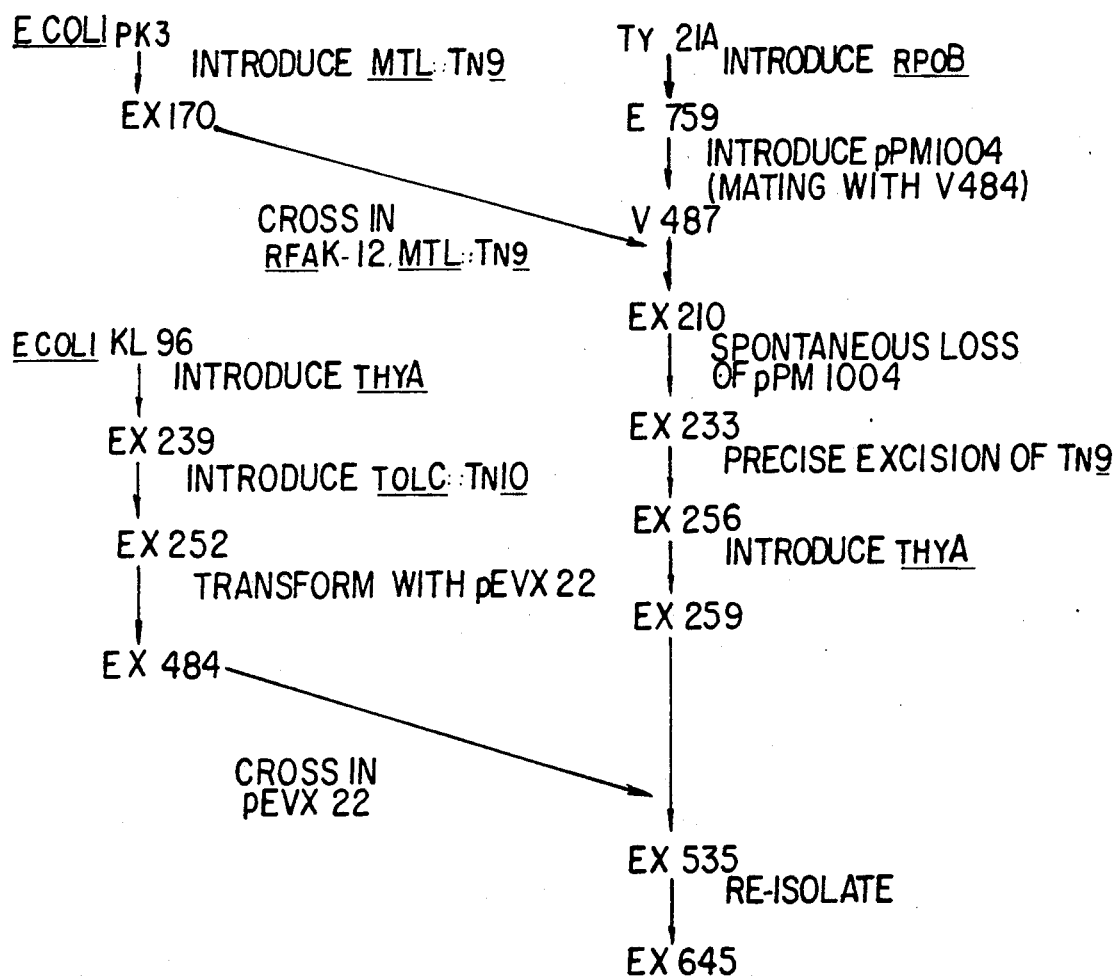

Table 1 includes the genotypes of strains used in the construction. FIG. 2 is a flow chart describing the vaccine construction. Each step of FIG. 2 is separately described below.

Step 1: Ty21a→E759

Strain Ty21a was spread on NA plates with rifampicin (100 μg/ml) and a rifampicin-resistant derivative was selected and called E759.

Step 2: E759→V487

Figure 3:
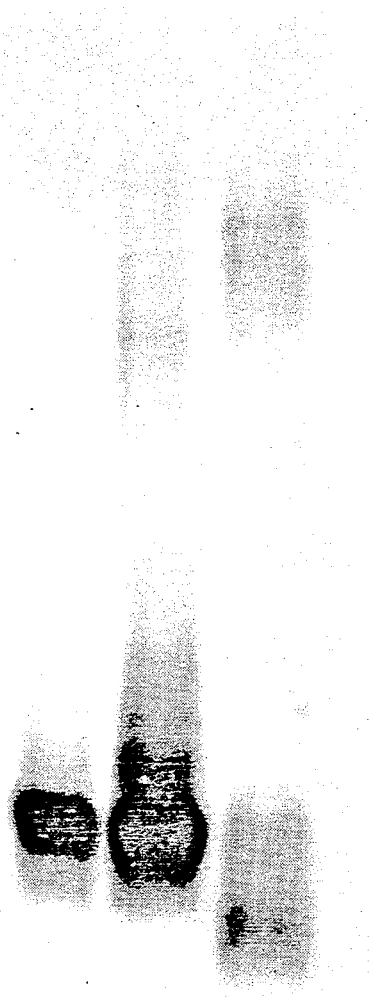
Figure 4:
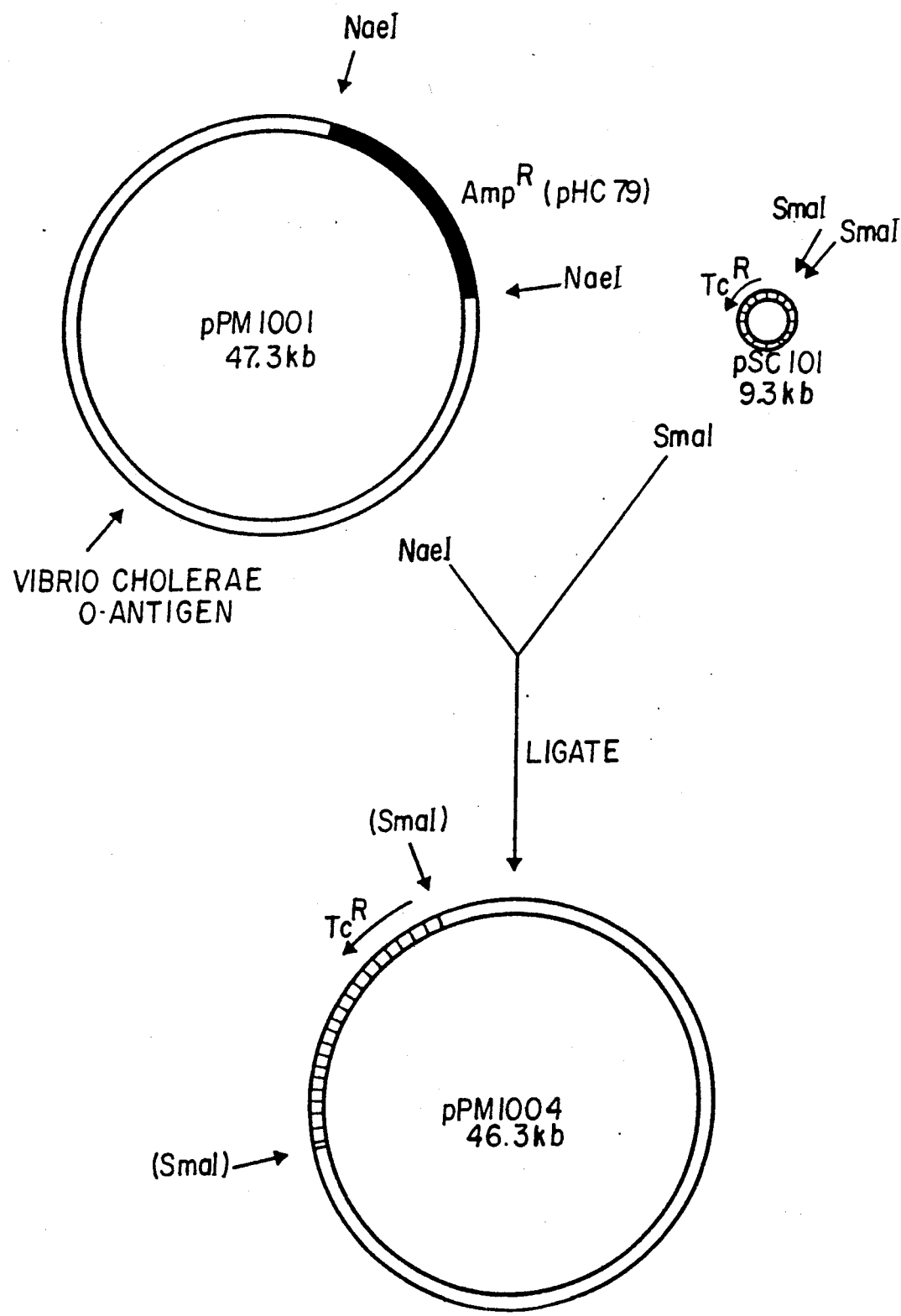
Figure 5:
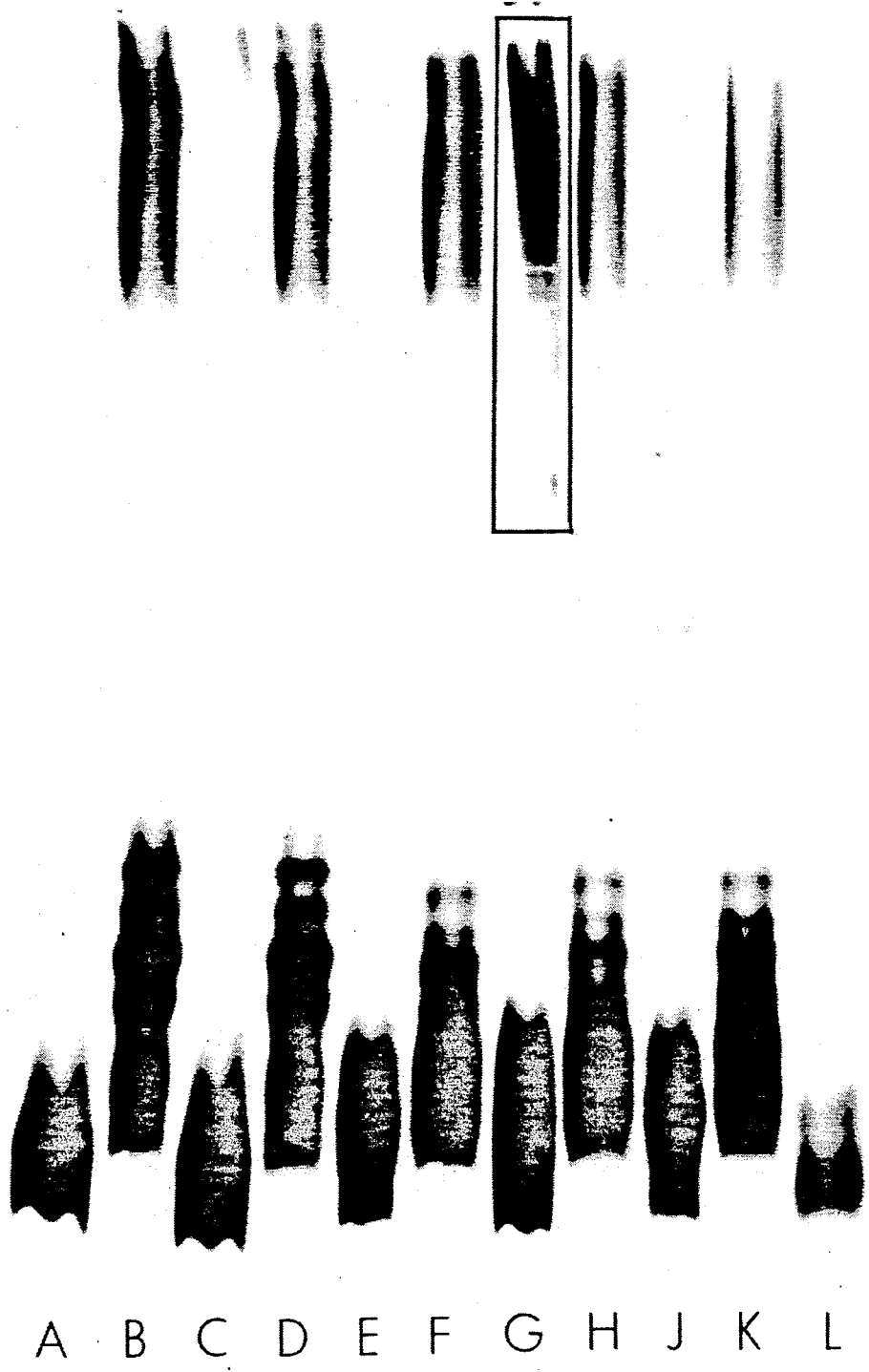

Strain V487 was constructed from strain E759 which received, by conjugation, a plasmid (pPM1004) specifying tetracycline-resistance, and carrying DNA from *V.cholerae* Inaba serotype sufficient, in *E.coli* K-12, to allow the synthesis of *V.cholerae*-like LPS by the recombinant (FIG. 3, track B). Plasmid pPM1004 (FIG. 4) carries most of the *V.cholerae* DNA originally cloned in pPM1001 (FIG. 4). Whilst *E.coli* K-12/pPM1004 produced LPS similar to that of *V.cholerae* (FIG. 3, tracks B & C), strain V487 did not. (FIG. 5, tracks C & D).

Step 3: V487→EX210

Figure 6:

The aim in the construction of strain EX210 was to introduce the rfa region of *E.coli* K-12 into the Ty21a background of the candidate vaccine strain, as it was thought that the good expression of *V.cholerae*-like LPS in *E.coli* K-12, and the apparent absence of such expression in Ty21a, may be due to the suitability of the *E.coli* K-12 LPS core as a substrate for O-antigen polymerisation in contrast with the lack of suitability of the *S.typhi* LPS core for this purpose. Thus strain EX210 is basically V487, but with the chromosomal rfa region of Ty21a replaced with the equivalent region from *E.coli* K-12. Strain EX210 was constructed by bacterial conjugation, with donor EX170 and recipient V487. The construction of the recipient, V487, has been described above (Step 2). The donor was designed to mediate Hfr transfer of the rfa region of *E.coli* K-12 to the recipient, with selection for a nearby mtl::Tn9 marker. Bacteriophage P1vir was grown on *E.coli* K-12 NK6701 (mtl::Tn9) and the chloramphenicol-resistance marker transduced to *E.coli* K-12 PK3 (Hfr P0131). The resulting strain (EX170) acted as a donor in an experiment in which an *E.coli* K-12 (rpsL) (strain P400) was the recipient; chloramphenicol-resistance and inability to ferment mannitol were co-transferred at high frequency. Strain EX170 was then used as a donor of mtl::Tn9 to V487, with selection for chloramphenicol-(mtl::Tn9), tetracycline- (pPM1004) and rifampicin-resistance (V487 background). About 50% of such exconjugants produced *V.cholerae*-like LPS as judged by SDS-PAGE. It was thought that such strains may possess the rfa region of *E.coli* K-12. In order to confirm that EX210 produced *V.cholerae*-like LPS, which was distinct from that of *S.typhi*, various strains were grown with or without galactose (galactose in the medium allows the production of O-antigen chains by *S.typhi* Ty21a) and the LPS synthesised by such strains were viewed on gels (FIG. 5). The core of strain EX210 has a mobility on SDS-PAGE distinct from that of the Ty21a core made in the absence of galactose (FIG. 5, compare tracks A or C with track E.). When the growth medium was supplemented with galactose, both Ty21a and EX210 were capable of the synthesis of long O-antigen chains characteristic of Salmonella (FIG. 5, compare tracks B and F). Note that the LPS ladders produced in the presence of galactose are out of register. This indicates a difference in the LPS molecules, and presumably reflects the LPS core difference. Strain EX210, but not strain V487, synthesised *V.cholerae*-like O-antigens in galactose-free growth media (FIG. 5, compare tracks C and E). To show that the *E.coli* rfa region had been transferred to *S.typhi* in the above experiment, the LPS core region from various strains was viewed on gels (FIG. 6). The lowest band in each gel track may represent the intact core of the strain (to avoid difficulty of interpretation with galE strains, all strains were grown with galactose). The lowest band seen in the EX256 and EX645 tracks had a mobility the same as that of the lowest band seen in the KL96 and EX170 tracks; the mobility of these bands differed from that of the lowest band in the Ty21a track. The gel also shows bands corresponding to core-attached groups (from 1 to 5) of *S.typhi* O-antigen units (*V.cholerae* O-antigen units would not be seen in track E, as EX645 was grown in nutrient broth with glucose as well as galactose, and glucose inhibits the production of *V.cholerae*-like LPS by EX645 growing in complex media). The mobilities of this group of bands are shifted down in tracks D and E, compared with track C, reflecting the polymerisation of the O-antigen units on different cores. The phage sensitivity pattern of various strains, using a bacteriophage (Felix-0) which employs the Salmonella LPS core as receptor, was examined. Strain EX210 was not lysed by the phage while the Ty21a was susceptible.

Step 4: EX210→EX233

As pPM1004 was not a suitable plasmid for use in a vaccine strain (due to expression of tetracycline-resistance) a spontaneous plasmid-free isolate of EX210 was obtained and called EX233. By agarose gel electrophoresis of a protein-free cell lysate, it was shown that no plasmid could be detected in EX233.

Step 5: EX233→EX256

In order to remove the chloramphenicol-resistance property (Tn9) from EX233, mtl+ revertants were obtained, and screened chloramphenicol-sensitive. One such strain was called EX256.

Step 6: EX256→EX259

A non-reverting thyA− mutation was introduced into EX256, to allow the selection, in a later step, of introduction of a thyA+ plasmid. The thyA− derivative of EX256 was called EX259. EX259 was the recipient of the recombinant plasmid pEVX22, to give the final vaccine strain: EX645. EX259 possessed an LPS core with mobility characteristic of EX210, did not produce *V.cholerae*-like LPS, but retained the capacity, when grown with galactose, to polymerise *S.typhi* O-antigen units on the core.

Figure 7:
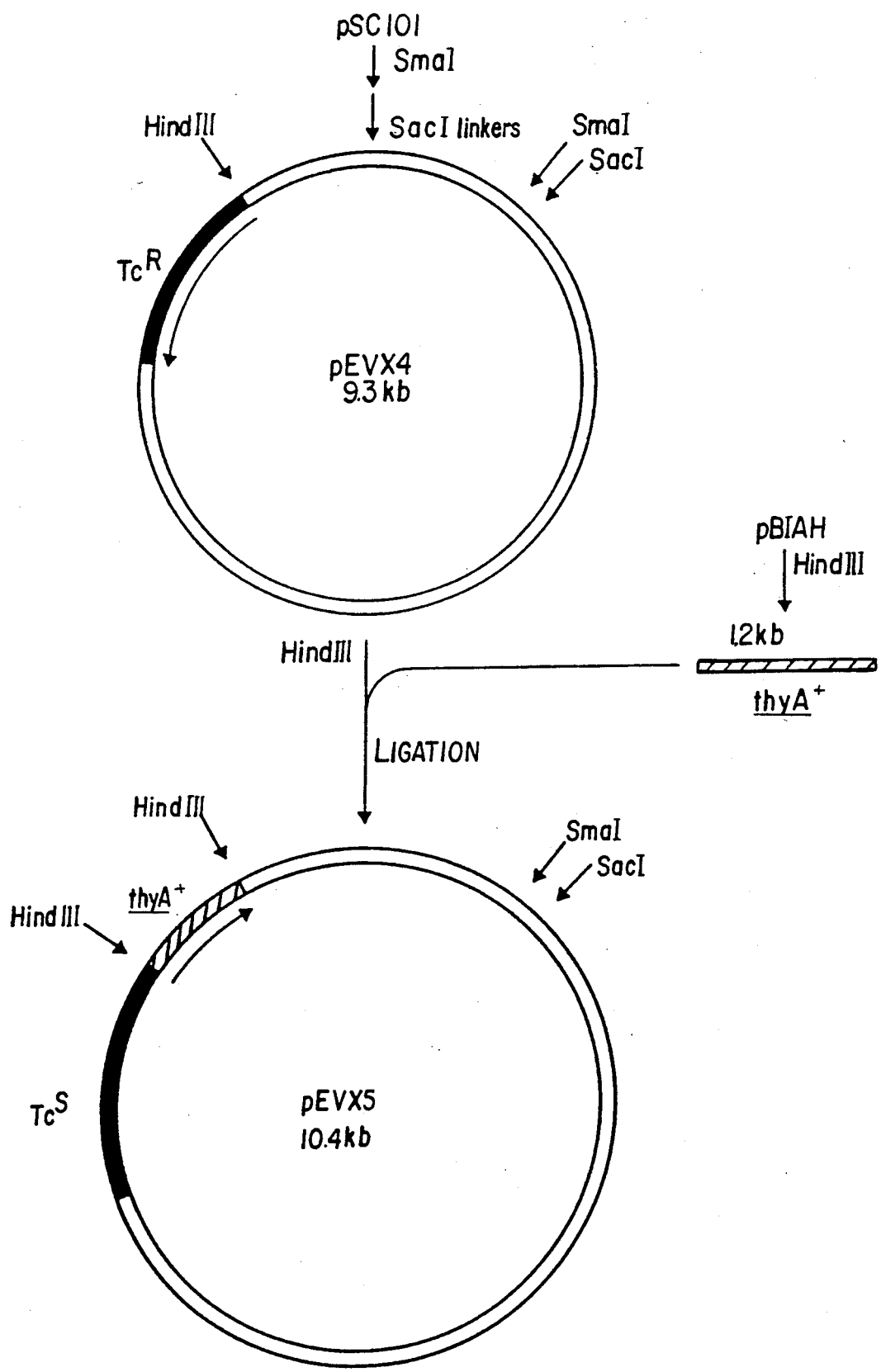
Figure 8:
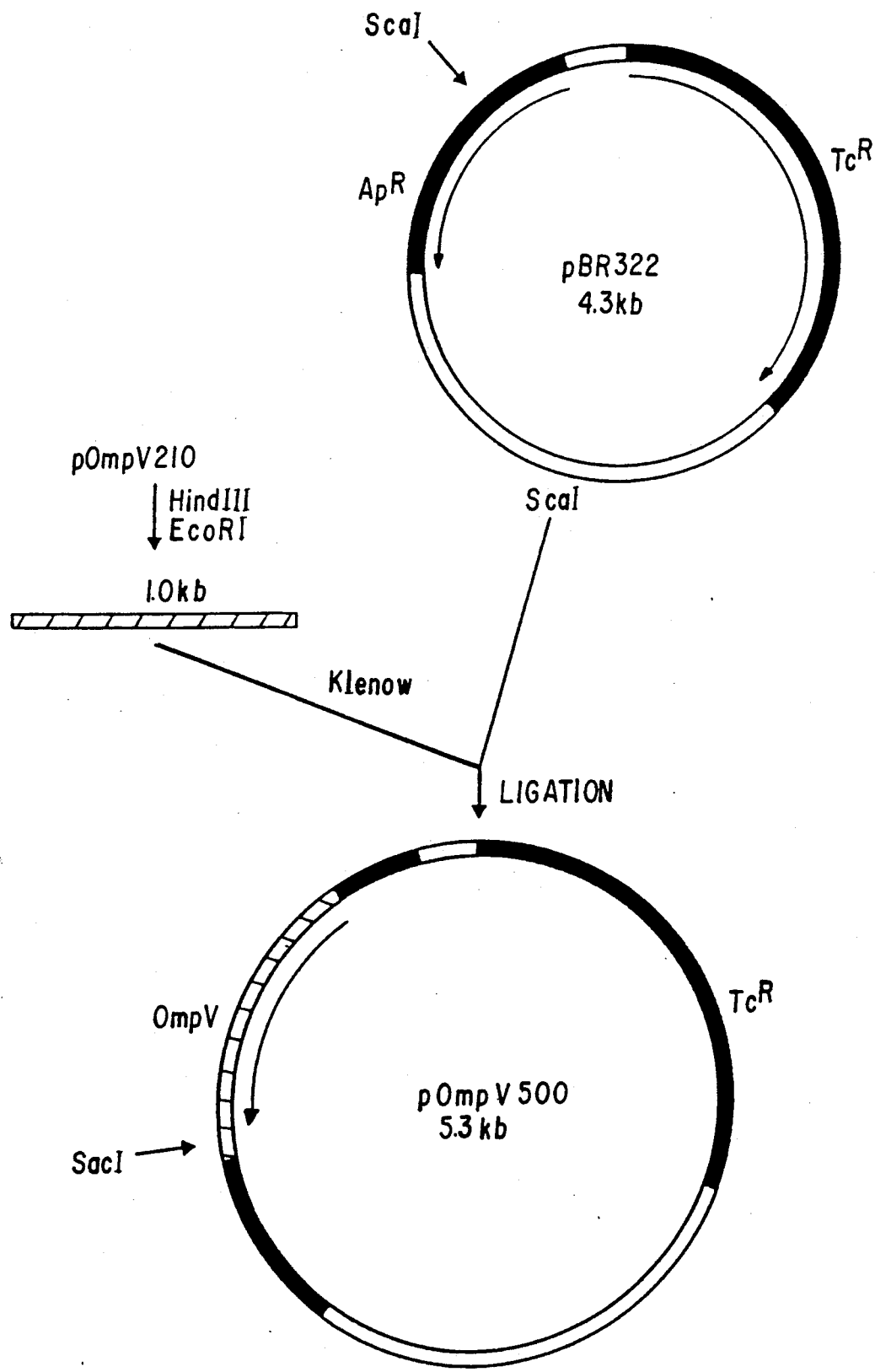
Figure 9:
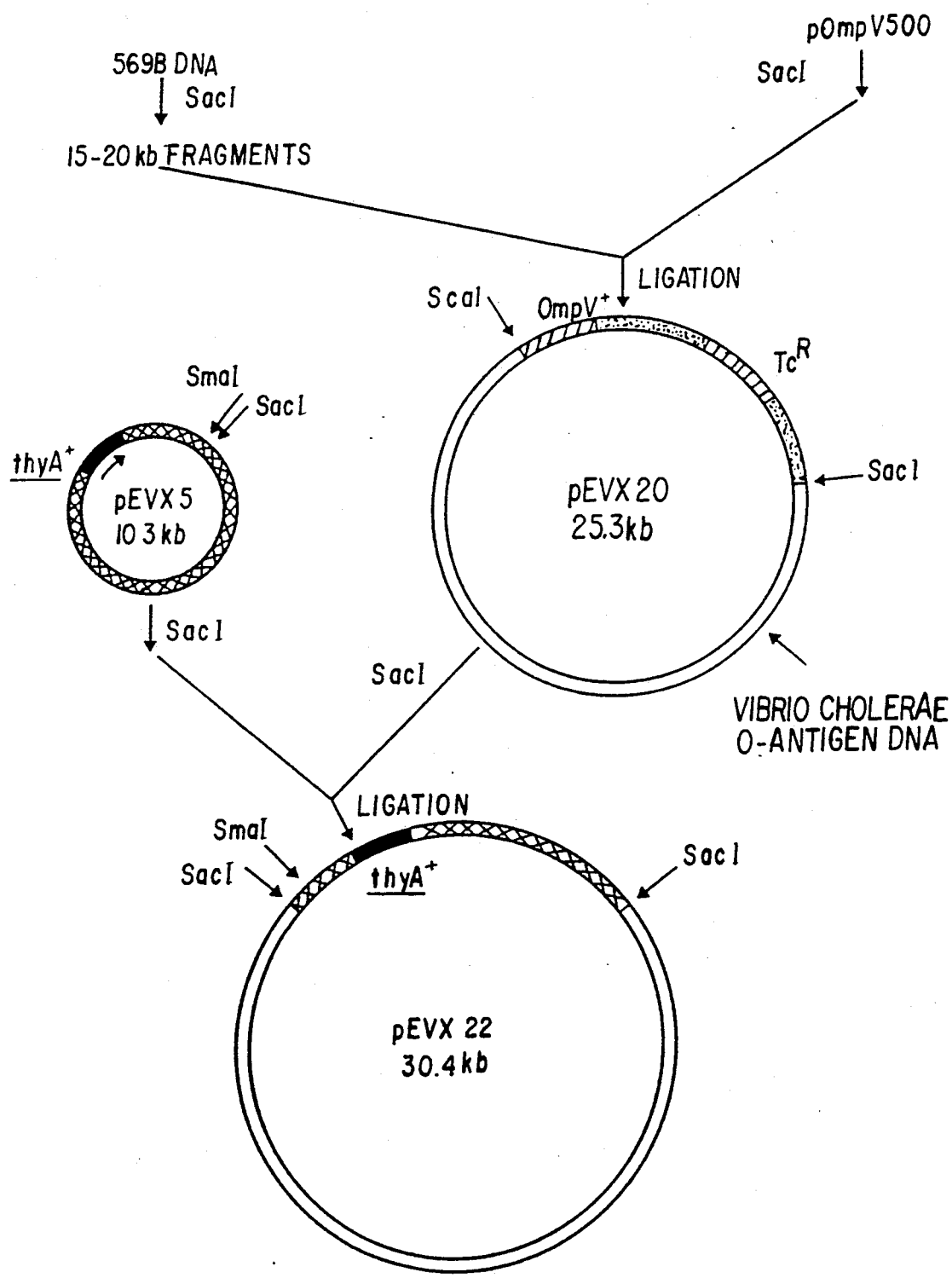

2. Construction of the recombinant plasmid expressing O-antigen biosynthetic cenes of V.cholerae The construction of the required plasmid is described (FIGS. 7 to 9). We obtained evidence which indicated that a SacI fragment of 20kb, from the chromosome of *V.cholerae* 569B (Classical, Inaba), could be expected to encode the necessary genes. Such a fragment was eventually obtained in the cloning vector pEVX5 (FIG. 9).

The final plasmid (pEVX22) carries the replicon of pSC101, a HindIII fragment of 1.12 kb from pBTAH encoding the thyA+ gene of E.coli K-12, and the necessary DNA from V.cholerae. The thyA+ HindIII fragment is inserted into the HindIII site in the promotor region of the tetracycline-resistance gene of pSC101 and the plasmid does not mediate high-level resistance to tetracycline.

2.1 Construction of pEVX5

The steps involved are shown in FIG. 7. Plasmid PEVX5 is derived from pSC101. In the first step of construction, a site was introduced into PSC101 by digestion of PSC101 with SmaI [pSC101 has 2 SmaI sites separated by 196bp, at positions 7327 and 7523 on the map, and ligation with SacI linkers. After SacI digestion, ligation, and transformation into DH1 (an *E.coli* K-12 strain) with selection for tetracycline-resistance, a plasmid was obtained which had a novel SacI site but retained a single SmaI site. This plasmid was stored as pEVX4. Plasmid pEVX4 was then digested with which cut in the promoter region of the tetracycline-resistance determinant, and ligated with a 1.12 kb HindIII fragment carrying the thyA+ gene of *E.coli* K-12, derived from pBTAH. The ligated mixture was transformed into a thyA− derivative of LE392 (EX98),with selection for thymine prototrophy. A plasmid of the expected structure (i.e. PEVX4 with a 1.12 kb HindIII fragment) was obtained, and stored as pEVX5.

2.2 Initial cloning of the requisite V.cholerae DNA

Chromosomal DNA from *V.cholerae* 569B was digested with SacI. and fragments 15–20 kb in size were prepared by fractionation on a sucrose gradient. The fragments were ligated to pOmpV500 (FIGS. 8 and 9). Plasmid pOmpV500 is a tetracycline-resistant PBR322-based plasmid, carrying a 1.0 kb HindIII fragment from pOmpV210 cloned into the SacI site of pBR322, and expressing the OmpV protein of *V.cholerae*. This plasmid ws chosen as an initial cloning vector because of its high copy-number, the presence of a SacI site and the ease of selection of recombinant plasmids using tetracycline-resistance (FIG. 8). Tetracycline-resistant transformants (into strain DH1) were screened by slide agglutination with an antiserum directed against *V.cholerae* 569B. Reactive clones had recombinant DNA of the expected structure (pOmpV500 with a 20 kb insert) and one was stored as pEVX20 (FIG. 8).

2.3 Construction of oEVX22

Plasmid pEVX20 was digested with SacI and ligated to SacI-cut pEVX5. After transformation into EX98, and selection for thymine prototrophy, the transformants obtained were screened by slide agglutination with the anti-*V.cholerae* 569B antiserum. Plasmids were prepared from reactive transformants, and one of the expected structure (pEVX5 with a 20 kb insert) was stored as pEVX22 (FIG. 9).

3. Construction of the recombinant vaccine strain EX645

This part describes the introduction of pEVX22 into the carrier strain EX259. Initial experiments in which we attempted to transform pEVX22 into EX259, with selection for thymine prototrophy, were unsuccessful. Hence, an *E.coli* K-12 Hfr strain, carrying pEVX22, was used as donor in a mating with EX259, and the plasmid was introduced by this means.

Step 1: Construction of a thyA− mutant of an Hfr E.coli K-12 strain→EX239

Strain KL96 was plated with thymine and trimethoprim, and a non-reverting thyA− derivative stored as EX239.

Step 2: Introduction of a counterselection marker into EX239→EX252

Strain EX239 served as recipient, in a Plvir transduction, of tetracycline-resistance from strain P2495 (tolC210::Tn10). The tolC genotype confers sensitivity to the detergent sodium deoxycholate at or above 0.05% w/v. A strain thus constructed was stored as EX252.

Step 3: Introduction of pEVX22 into EX252→EX484
Strain EX252 was transformed with pEVX22, with selection for thymine prototrophy. A transformant was purified and stored as EX484.

Step 4: Introduction of pEVX22 into EX259→EX645

Strain EX484 served as donor in a mating with EX259. Exconjugants, which were obtained at a frequency of 1 in $10^9$, were selected on sodium deoxycholate and rifampicin, with selection also for thymine prototrophy. One such strain was stored as EX535. After storage at −70° C. for 1 year, the viability of the strain was reduced. A single colony isolate from the storage vial was amplified on selective plates and lyophilised in a cellbank as EX645. This is our candidate vaccine strain.

CHARACTERISATION OF STRAIN EX645

1. Summary

We sought to characterise strain EX645 in some detail. A summary of the work is presented here and later sections describe the work in detail. Work was performed on bacteria grown from the cellbank, except where otherwise indicated.
(a) Strains of Ty21a and EX645 are identical in the following characteristics:
appearance
inability to ferment galactose,
inability to produce $H_2S$,
API 20E Enterobacteriaceae Typing System Profile,
auxotrophies
sensitivity to a variety of antibiotics,
levels of Leloir enzymes produced, and
outer membrane protein profiles on SDS-PAGE.
(b) Strain EX645 carries a recombinant plasmid which is responsible for the synthesis of a *V. cholerae*-like O-antigen as judged by SDS-PAGE and haemagglutination-inhibition data. Restriction enzyme digests of the plasmid DNA show the expected structure. The plasmid carries little *V. cholerae* DNA which is unnecessary for *V. cholerae* O-antigen synthesis. The plasmid does not carry *V. cholerae* DNA homologous to the LT-B toxin DNA of *E. coli*.
(c) The minimal inhibitory concentration (MIC) of tetracycline for EX645 is 4 μg/ml; the MIC for Ty21a is 2 μg/ml. There is low-level reversion (1 in $10^9$) of EX645 to high-level tetracycline-resistance.
(d) In vitro tests have shown that the plasmid of EX645 does not transfer to *E. coli*. The vector pSC101, which is the basis for the plasmid of EX645 is a low mobilisation vector and transfer would be expected to be a rare event. The in vivo experiments of Levine et al using model systems have shown that in the absence of external selection pressure, transfer of plasmids in vivo is a rare event. The *E. coli* K-12 DNA in the rfa region of EX645 is unlikely to transfer to other organisms.

(e) The plasmid is not fully stable in the absence of selection (i.e. in the presence of thymine). Bacteria which have lost plasmid (thyA$^-$) may be viewed as having acquired yet another attenuating marker.

2. In vitro tests with Ty21a and EX645

The in vitro tests described in 2.1, 2.2 and 2.3 below were performed on EX645 grown from the master cellbank in order to characterise EX645 by comparision with its parent Ty21a. These tests are based on "Requirements for Typhoid Vaccine (Live Attenuated, Ty21a, Oral)" of the WHO Expert Committee on Biological Standardisation.

2.1 Strain Characterisation (a) Description

When grown in Brain Heart Infusion (BHI) broth and subsequently examined, both Ty21a and EX645 are Gram-negative rods and motile.

(b) Slide agglutination reactions

Organisms grown for 3 passages in BHI broth in the presence and absence of galactose added to the rate of 1 gm/liter, gave the following results on slide agglutination.

|  | H:d | Vi | 0:9 | 0:12 | Inaba | Ogawa |
|---|---|---|---|---|---|---|
| Absence of galactose |  |  |  |  |  |  |
| Ty21a | + | − | +/− | + | − | − |
| EX645 | + | − | +/− | + | + | − |
| Presence of galactose |  |  |  |  |  |  |
| Ty21a | + | − | ++ | +++ | − | − |
| EX645 | + | − | ++ | +++ | + | − |

(c) Ability to ferment galactose

When grown on Bromothymol Blue agar supplemented with 1 gm/liter galactose, the vaccine strain ($10^{12}$ organisms) did not produce colonies able to ferment galactose (i.e. calE+ revertants).

48 hours incubation 7 days incubation Ty21a no revertants, no lysis no revertants EX645 no revertants, no lysis no revertants (d) Production of H$_2$S When grown on Kligler iron agar slants neither Ty21a nor EX645 showed blackening, indicating that no H$_2$S was produced.

(e) Biochemical profile

When tested using the API 20E Enterobacteriaceae Typing System, both Ty21a and EX645 yielded the same biochemical profile. Ty21a Profile 4004500 identifies S.typhi EX645 Profile 4004500 identifies S.typhi (f) Auxotrophies Both Ty21a and EX645 require L-valine and L-isoleucine to support growth. Both organisms will grow in a medium consisting of inorganic salts, dextrose and these two amino acids. No other growth requirements have been identified.

(g) Antibiotic sensitivity

Antibiotic sensitivity was assessed by using antibiotic sensitivity test discs placed onto seeded agar plates.

| Antibiotic | Ty21a | EX645 |
|---|---|---|
| Ampicillin (2 µg) | sensitive | sensitive |
| Chloramphenicol (10 µg) | sensitive | sensitive |
| Kanamycin (30 µg) | sensitive | sensitive |
| Tetracycline (10 µg) | sensitive | sensitive* |
| Streptomycin (25 µg) | small zone | resistant |
| Rifampin (2 µg) | small zone | resistant |

*Although EX645 is tetracycline sensitive by this measure there is a low level reversion to tetracycline resistance (refer 1.(c)).

2.2 Leloir Enzyme activities

Figure 10:
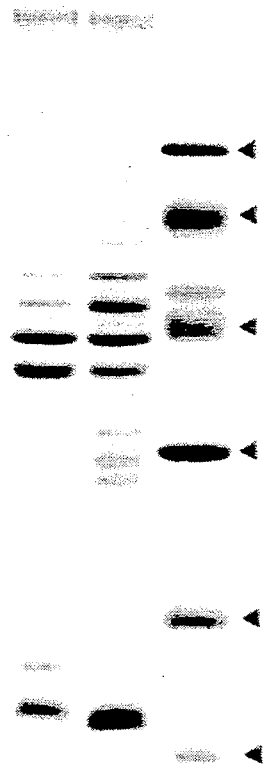
Figure 11:
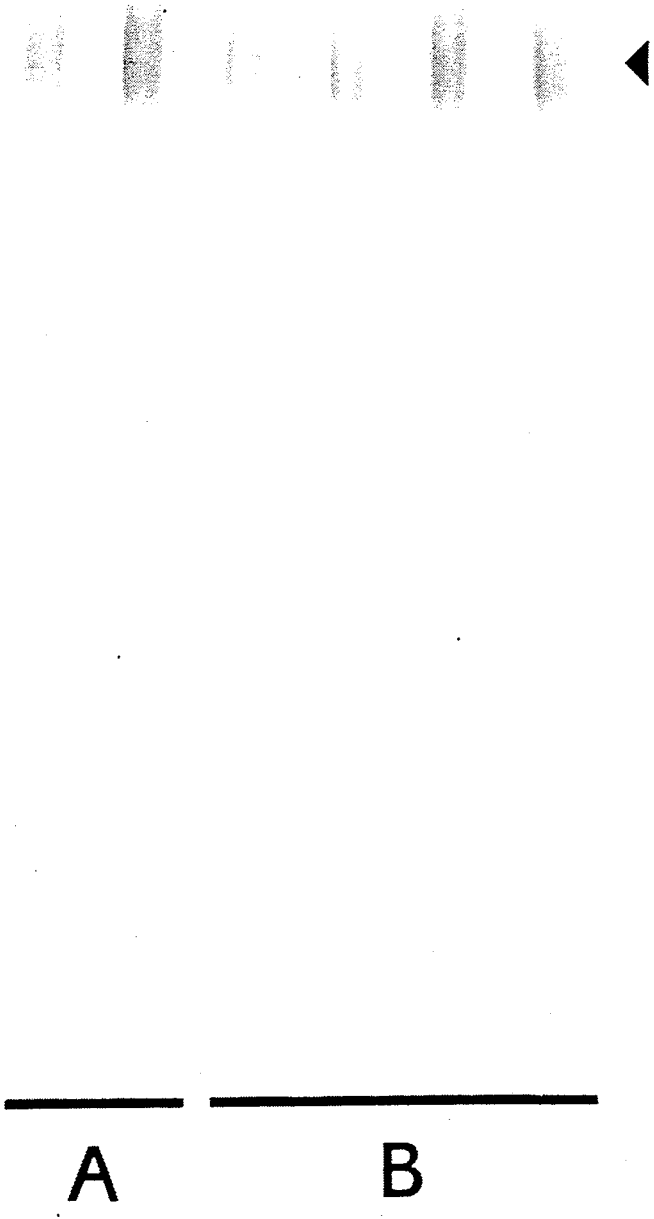

Both Ty21a and EX645 had similar activities of the Leloir enzymes encoded by the galT and galK genes (Table 2); neither strain expressed detectable galE enzyme activity. The cell membrane protein profiles of the 2 strains appeared identical on SDS-PAGE (FIG. 10). Cells of Ty21a and EX645. were pulse-labelled with [$^{14}$C]-galactose, and the labelled LPS was viewed by autoradiography (FIG. 11). There was no obvious difference in the LPS profiles of the strains. Each strain incorporated [$^{14}$C]-galactose into high molecular weight Salmonella LPS, a phenotype typical of galE$^-$ mutant strains.

2.3 Galactose-induced bacteriolysis

When grown in shake flasks in BBL Infusion broth, supplementation with dextrose-free galactose induced lysis of Ty21a at additions ranging from 1% to 10% galactose by weight. Under the same conditions, EX645 exhibited a retarded rate of growth but did not lyse.

The plasmid of EX645

Figure 12:
Figure 13A:
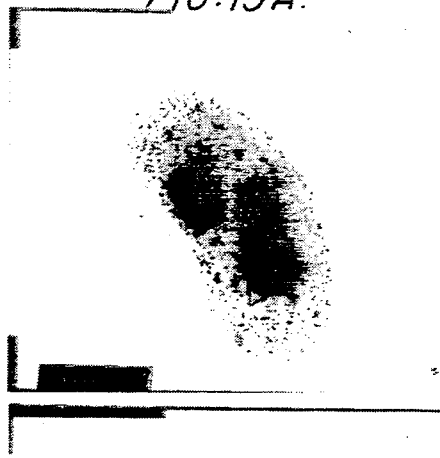
Figure 13B:
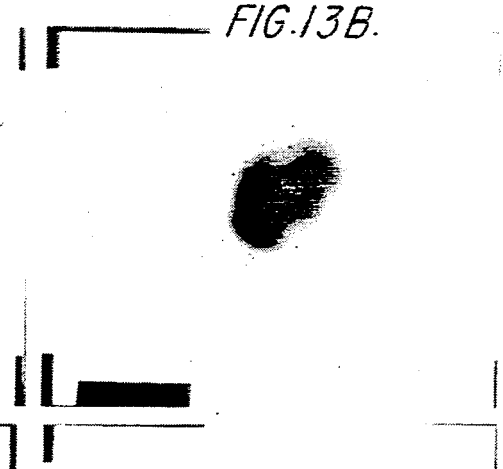
Figure 13C:
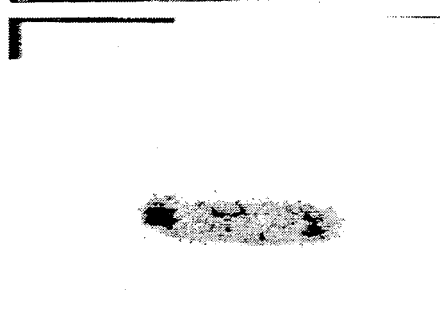
Figure 13D:
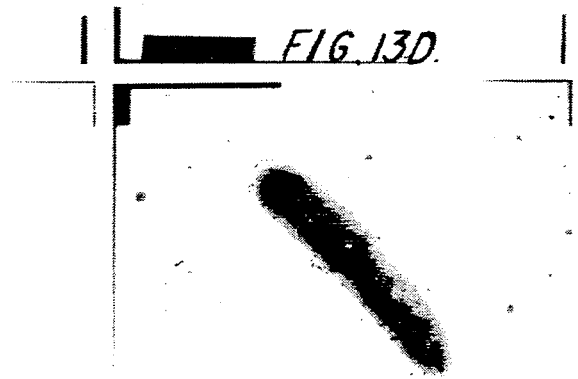
Figure 13E:
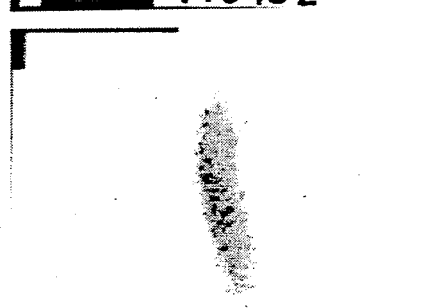
Figure 13F:
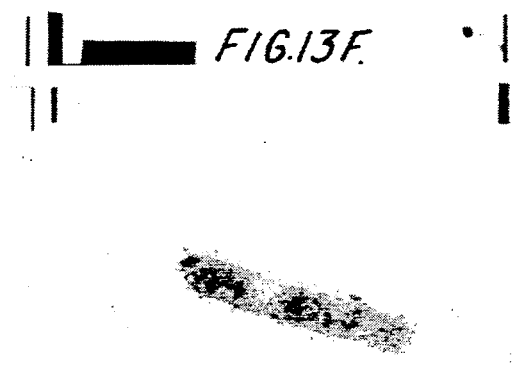
Figure 13G:
Figure 13H:
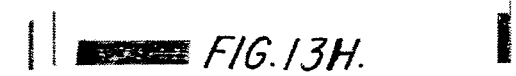

Strain EX645, grown in galactose-free medium, synthesised LPS similar to the LPS of *V.cholerae* by SDS-PAGE (FIG. 5) and immunoblot (FIG. 12). A gel such as that shown in FIG. 5 was run, the material transferred to nitrocellulose, and subjected to immunoblot using an anti-*V.cholerae* antiserum. Strain EX645, grown in the absence of glucose, made material identifiable as *V.cholerae*-like LPS (FIG. 12, tracks A & C).

To demonstrate that the *V.cholerae*-like LPS made under these conditions was surface-associated, and that both *S typhi* LPS and *V.cholerae*-like LPS could be demonstrated on EX645 under certain growth conditions, we used immunogold electron microscopy (FIG. 13). The use of specific anti-[*V.cholerae* LPS] antibody (mouse monoclonal anti-C) or polyclonal anti-[*S.typhi*] serum first demonstrated the specificity of the sera (FIG. 13, panels A to D). Strain EX645 grown in the absence of galactose synthesised *V.cholerae*-like LPS but did not make smooth *S.typhi* LPS (FIG. 13, panels E and F). When galactose was present during growth, LPS of both types was made (FIG. 13, panels G and H). Although glucose was also present during growth of bacteria for panel G, *V. cholerae*-like LPS may be detected as its production is not inhibited in glucose-supplemented minimal medium, unlike the effect seen when growth occurs in glucose-supplemented non-defined medium. Bacteria grown as for panels G and H were screened, in the electron microscope, to estimate the number of bacteria capable of the production of both *S.typhi* LPS and *V.cholerae*-like LPS under these conditions. Essentially 100% of the cells bound antibody to *S.typhi* LPS. Differential plate counts gave the percentage of thyA+ (plasmid pEVX22-containing) bacteria in the culture as 76%. Hence, about 70% of the bacteria expressed both *S.typhi* LPS and *V. cholerae*-like LPS (FIG. 14).

The amount of such LPS made under varying growth conditions was quantitated by haemagglutination inhibition (Table 3). In the absence of galactose, EX645 appeared to produce some *V.cholerae*-like LPS, organism for organism about 50% of that found for *V.cholerae* 569B. In the presence of excess galactose, *V.cholerae*-like LPS could not be detected on the strain, possibly due to masking of the shorter *V.cholerae*-like material by longer *S.typhi* O-antigen chains. When limiting amounts of galactose were used, both *V.cholerae*-like LPS and *S.typhi*-like LPS could be detected on EX645.

Plasmid (pEVX22) was prepared from EX645 and mapped with a variety of restriction enzymes (FIG. 15). Single or double digests of either pEVX22 or vector pEVX5 yielded fragments of the expected sizes, as judged by the known sequence of pSC101, the known structure of pEVX5 (FIG. 7), and the Published map of the analogous *V.cholerae* DNA encoding the O-antigen of *V.cholerae* 017 (El Tor, Ogawa). Reproductions of some digests are shown, FIGS. 16 to 18). Of particular note is the presence of the 1.12 kb HindIII thyA+ fragment of pBTAH in both pEVX5 and PEVX22 (FIG. 16, tracks 8 to 10). Table 4 lists the numbers of sites seen on some digestions of interest.

Experiments in which the closely analogous 20kb SacI fragment of pEVX7 derived from the El Tor, Ogawa strain *V.cholerae* 017, was subjected to deletion mutagenesis (FIG. 19) showed that the 20 kb SacI fragment of the *V.cholerae* chromosome adequate for O-antigen biosynthesis is close to minimal in size. In particular, deletions A and D of FIG. 19 demonstrated that DNA within 2–4 kb of either .end was required for function.

Various strains, grown on a nitrocellulose filter, were probed with a radiolabelled DNA fragment encoding the LT-B subunit of *E.coli* enterotoxin (FIG. 20, A). Homology between the DNA of some strains and the probe was evident. *V.cholerae* 569B hybridised well with the probe but EX645 did not. In a control experiment, radiolabelled pADE107 (carrying the gal DNA of *S.typhimurium*) was used to probe a similar filter (FIG. 20, B). Strains negative on toxin probing were positive here, showing that DNA from the lysed toxin-negative strains had successfully bound to the filter.

4. Sensitivity to tetracycline of strain EX645

The MIC of tetracycline for Ty21a was 2 μg/ml, while EX645 had an MIC of 4 μg/ml. When EX645 was plated on NA with tetracycline (12 μg/ml), tetracycline-resistant revertants arose al about I in $10^9$.

5. Transfer of plasmid or E.coli K-12 DNA

As strain EX645 differed from Ty21a by addition of new DNA (from *E.coli* K-12) in the mtl region, and by the possession of a recombinant plasmid, it was necessary to show that neither DNA fragment could be transferred to other organisms under conditions where EX645 was in proximity to a strain receptive to conjugation.

5.1 Transfer of pEVX22

A filter mating was performed between EX645 and *E.coli* K-12 strain EX691 (thy−), with selection for plasmid-containing exconjugants on minimal medium supplemented with glucose as carbon source, and with methionine as the only other supplementation. This medium counterselected the donor (EX645 is ilv−),but would allow growth of thyA+ (i.e. pEVX22-containing) derivatives of EX691. When $10^{10}$ of EX691 were mixed with $10^9$ of EX645 in this experiment, no thyA+ exconjugants were detected. Plasmid transfer in this experiment was therefore <1 in $10^9$.

5.2 Transfer of chromosomal DNA in the mtl-rfa region

As EX645 did not contain an easily selectable marker in the mtl-rfa region, EX233 (a precursor of EX645, with mtl::Tn9) was used as a donor in a mating with EX691, as described above. Selection was on minimal medium with methionine, and thymine, also supplemented with chloramphenicol. Bacteria able to grow on these plates would be chloramphenicol- resistant derivatives of EX691 (the donor, EX645, is counterselected here by absence of supplementation to relieve the ilv− defect). In an experiment where $10^{10}$ of EX691 bacteria were available as recipients, no chloramphenicol-resistant derivatives were detected. The transfer of the mtl::Tn9 marker in this test was therefore <1 in $10^9$.

Rules governing work with rDNA molecules precluded experiments in which transfer of pEVX22 from EX645 into species of bacteria other than *E.coli* and Salmonellae could be examined. We would expect, however, that such transfer would not occur. Strain EX691 is rough (which would increase recipient ability over that of an otherwise isogenic smooth strain), is F−, and is restriction negative. It would therefore be expected to be particularly effective as a recipient in conjugation.

5.3 Other consideration

The in vivo studies conducted by Levine et al demonstrated that a Poorly mobilisable or "safe" plasmid, pBR325, did not transfer after ingestion by volunteers of a normal human flora strain of *E.coli* K-12 carrying the plasmid, in the absence of a derepressed conjugated plasmid (F-amp) and concomitant selection pressure, i.e. co-administration of tetracycline. Transfer occurred only in the presence of both of these selection factors.

The base cloning vector (pSC101) in our plasmid pEVX22 is considered to be poorly mobilisable and could be expected to behave similarly to pBR325. In the absence of a convenient selection marker, such as antibiotic resistance, in vivo studies of transfer of pEVX22 are not possible.

As documented elsewhere, the recombinant plasmid is not fully stable in EX645, however, loss of plasmid would result in a thyA− genotype which would further reduce the virulence of the strain owing to the low concentrations of thymine in body fluids. It is also necessary to consider the possibility that the thyA− mutation of EX645 could transfer to other organisms, thereby rendering them trimethoprim-resistant. Spontaneous mutation to thyA− occurs (in *E.coli* K-12 and Salmonella) at about 1 in $10^6$, while mobilisation of a chromosomal marker from EX645 to an *E.coli* K-12 strain occurred at <1 in $10^9$ (above). If it is assumed (as is likely) that most organisms may mutate to thyA− at about 1 in $10^6$, then any transfer of the vaccinal thyA− marker to other enteric or environmental bacteria is of no possible significance.

EXAMPLE 5

CHALLENGE TRIALS

This example reports on a cholera challenge trial conducted at the Center for Vaccine Development at the University of Maryland at Baltimore in the United States using the Enterovax vaccine strain EX645.

TEST PRODUCT
Name: Evax CTV (EX645) Lyophilised Cholera/ Typhoid Vaccine
Dosage Form: Single dose vials containing lyophilised vaccine organisms for reconstitution and oral administration
Dosage:
Dose 1 & Total organisms $3.7 \times 10^{11}$/dose
Dose 2 Viable organisms $2.7 \times 10^{10}$/dose
Viable organisms carrying plasmid $1.54 \times 10^{10}$/dose
Dose 3 Total organisms $2.85 \times 10^{11}$/dose
Viable organisms $1.11 \times 10^{10}$/dose
Viable organisms carrying plasmid $1.03 \times 10^{10}$/dose
Batch Nos. Dose 1 & Dose 2 8F036E
Dose 3 8F037E
Date of 8F036E January, 1988
Manufacture: 8F037E February, 1988
No of Subjects: 8 vaccinees
13 controls CHALLENGE DOSE
Name: *Vibrio Cholerae* N16961 (El Tor, Inaba)
Dosage Form: Freshly grown organisms harvested and diluted in normal saline for oral administration.
Dosage: $1.07 \times 10^6$ cfu/dose

PURPOSE

The purpose of this study was to evaluate the cholera/typhoid hybrid vaccine - Evax CTV (EX645) Lyophilised Vaccine for safety, immunogenicity and efficacy in volunteers.

I. SYNOPSIS OF PROTOCOL

1. SELECTION OF VOLUNTEERS

Volunteers for these studies were healthy young adults recruited from the Baltimore Washington metropolitan area. They were selected on the basis of general good health, expressed interest and comprehension of the study as determined at a Preliminary interview. They must have had:
(a) No clinically signifcant history of cardiovascular disease, respiratory disease, endocrine disorder, liver disease including a history of hepatitis, renal and bladder disease, enlarged prostate, gastrointestinal disease, disorder of the reticuloendothelial system, neurologic illness, psychiatric disorder requiring hospitalisation.
(b) Normal and regular bowel habits falling within limits defined for a normal population: at least three stools per week and less than three stools per day without frequent use of laxatives or antidiarrheal agents.
(c) Absence of allergy to tetracycline.
(d) No history of antibiotic therapy during the seven days before the study.
(e) A negative pregnancy test:
(f) A negative HIV antibody test.

2. MEDICAL SCREENING AND CARE OF VOLUNTEERS

Prospective volunteers were carefully screened before the study to ensure that participating volunteers were in excellent health. The screening procedure included:
(a) Medical history
(b) Physical examination
(c) Electrocardiogram
(d) Urinalysis
(e) Complete blood count including platelet estimate
(f) BUN and fasting blood glucose
(g) VDRL
(h) Hepatitis B surface antigen
(i) HIV antibody
(j) Pregnancy test (women)
(k) SGOT and SGPT
(l) Psychological examination and interviews.

During hospitalisation on the Isolation Ward, oral temperatures were taken every eight hours; volunteers were examined and interviewed daily by physicians during the study.

Any volunteer who developed watery diarrhea had the stool volumes measured. Careful records of fluid intake and output were kept, and specific gravity was measured on all urine specimens passed.

If any volunteer developed copious watery diarrhea and was unable to maintain full hydration by oral means, intravenous replacement was given with polyelectrolyte fluids. Nurses and physicians were experienced in treatment of diarrheal disease including cholera, shigellosis, *E. coli*, and viral diarrhea.

3. STUDY DESIGN (a) Vaccination

A group of 14 volunteers were admitted to the Isolation Ward. Three doses of approximately $1 \times 10^{10}$ of the Ty21a/Inaba vaccine strain EX645 were given orally on days 0, 2 and 4. The vaccine stain was lyophilised and packaged in single dose vials and reconstituted in 30 ml of normal saline. Volunteers then drank 100 ml of distilled water. Volunteers ingested 2 gm of sodium bicarbonate in 50 ml of water five minutes before ingesting the vaccine strain. Volunteers had nothing by mouth for 8 hours before and 90 minutes after vaccination. Volunteers remained on the ward until stool cultures were negative for the vaccine strain.

(b) Challenge

Four to six weeks after vaccination, eight (8) vaccinees and thirteen (13) unvaccinated volunteers were admitted to the Isolation Ward. They were challenged with $1.07 \times 10^6$ V. cholerae N16961 (El Tor, Inaba). They were retained in the Isolation Ward for ten days in order to record symptoms and signs of gastrointestinal illness, to treat illness with appropriate hydration and support, and to perform bacteriological and immunological studies as outlined below. All volunteers were treated with tetracycline 500 mg qid for 5 days to eradicate the challenge organism from their stools before discharge.

4. PREPARATION OF INOCULA

The challenge strain was stored frozen in TSB with 15 percent glycerol. A vial of the challenge strain was thawed and streaked onto a Brain Heart Infusion (BHI)

agar plate. After 18 hours incubation at 37° C., 20–30 colonies that agglutinated with 01 and Inaba antisera were picked and used to heavily inoculate BHI agar plates for incubation at 37° C. for 18 hours. The organism (20–30 colonies) was replated, incubated for 5 hours, harvested with saline, and diluted in saline. Inoculum size was quantitated by replica spread-plate technique before and after challenge. The final inoculum was examined with Gram strain and agglutinated with specific antiserum.

5. INOCULATION OF VOLUNTEERS

The *V. cholerae* challenge strain was given by the oral route. Two grams of $NaHCO_3$ was dissolved in 5 ounces of distilled water. Volunteers drank 4 ounces of the $NaHCO_3$ solution; one minute later the volunteers ingested the $1.07 \times 10^6$ *V. cholerae* suspended in the remaining 1 ounce of $NaHCO_3$ solution. Volunteers took no food or water for 8 hours before and 90 minutes after inoculation.

6. PROCEDURE (a) Stool Specimens

A record was kept of the number, consistency, and description of all stools passsed by volunteers. A specimen of every stool was collected daily for culture (or a rectal swab if stool was not passed). If diarrhea occurred, stools were collected in a diarrhea seat for measurement of volume. Stools were treated with alphabenzyl chlorophenol for five minutes before flushing.

Stools were graded on a five point system:
grade 1 - firm (normal)
grade 2 - soft (normal)
grade 3 - thick liquid (abnormal)
grade 4 - opaque watery (abnormal)
grade 5 - rice water (abnormal)

All stools and duodenal strings after vaccination were inoculated onto Oxoid Nutrient Agar plates containing 100 µg/ml of rifampicin and 50 µg/ml of thymine and incubated for 40 hours at 37° C. Samples were also enriched using Oxoid Nutrient Broth No. 3 containing 100 µg/ml of rifampicin and 50 µg/ml of thymine and incubated for at least 16 hours at 37° C. Each broth was sampled and plated as described above. Growth was confirmed as being EX645 using slide agglutination with an anti-Ty2 Vi antiserum and an anti-*V. cholerae* 569B antiserum. All stools and duodenal strings after challenge were plated directly onto TCBS agar and inoculated into alkaline peptone water enrichment broth for overnight incubation prior to plating onto TCBS. Two stools each day (until antibiotic therapy began) were cultured quantitatively to determine the number of challenge organisms/gm stool.

(b) Blood

Serum samples were collected before vaccination and on days 7, 14 and 28 after vaccination and before challenge and on days 10, 21 and 28 after challenge. Sera were assayed for vibriocidal antibodies as well as for *S. typhi* and *V. cholerae* LPS antibodies. Twenty ml of heparinized whole blood was drawn for cellular immunity studies. Not more than 450 ml of blood was taken from any volunteer throughout the course of the study.

(c) Jejunal fluid

Volunteers were intubated before vaccination and again on about day 14 post-vaccination to collect jejunal fluid for estimation of local antibody production after vaccination. Volunteers swallowed polyvinyl chloride intestinal tubes to a distance of 130 cm from the mouth for collection of intestinal fluid to measure specific local sIgA antibody. Placement of the tubes in the proximal jejunum was verified by distance (130 cm) and colour (yellow-green) and pH of aspirated fluid. At least 40 ml of intestinal fluid was removed. Half the fluid was heated to 60° C. for 30 minutes in a water bath to inactivate complement before storage at $-70°$ C. The remainder of the fluid was similarly stored untreated.

(d) String capsules

To culture the vaccine or challenge strains from the proximal small intestine (the site of host-parasite interaction in the pathogenesis and immunity to cholera), volunteers ingested gelatin-encapsulated string devices (Enterotest) approximately 20 and 44 hours after each dose of vaccine or after challenge. Volunteers fasted from midnight to 6 am, and the string capsule was swallowed at 6 am and removed at 10 am. Volunteers were given only water while the strings were in place. In the stomach the gelatin capsule was digested and the nylon string unfurled. (In 95% of instances the string passes through the pylorus into the duodenum within four hours where it becomes impregnated with bile and duodenal material.) After four hours the strings were removed and the colour and pH of the distal 15 cm was recorded. If the pH was $\geq 6$ or the string was bile-stained, this provided evidence that the string had reached the duodenum. The distal 15 cm of the string was cut with a sterile blade, placed in a sterile container, labelled, and sent for bacteriologic culture.

II RESULTS

1. CLINICAL COMPLAINTS

Three subjects (3/14) complained of side-effects after a single dose (3/42) during the vaccination phase.
Two subjects complained of mild nausea after the first dose of vaccine.
Another subject complained of anorexia, malaise, abdominal gurgling and cramps and nausea. These symptoms were all of mild-moderate severity, commencing approximately 2 hours after the second dose, lasting about 3 hours.

2. IMMUNE RESPONSE DETAILS

The immune responses for volunteers after vaccination are shown in Tables 5 to 10.

2.1 Vibriocidal Assay Results

The vibriocidal antibody response measured by two assays at two different institutions were consistent. By the Center for Vaccine Development technique, 5 (36%) out of 14 recipients of EX645 had at least 4-fold rises in vibriocidal antibody to *V.cholerae* 01 Inaba at day 14 (Table 5). An additional seroconverter was identified using the vibriocidal assay performed using the Enterovax Limited technique, making the seroconversion rate 43% (Table 6).

2.2 Serum IgG and IgA Results

After vaccination, 1 (7%) of 14 vaccinees had 4-fold rises in serum IgG against Inaba LPS and 1 (7%) of 14 had a 4-fold rise in IgA against Inaba LPS (Table 7). Fourteen (100%) of 15 vaccines had 4-fold rises in IgG and anti-*S.typhi* and 10 (71%) of 14 had 4-fold rises in IgA anti-*S.typhi* LPS (Table 7).

2.3 Jejunal Fluid IgA Results

After vaccination, 1 (7%) of 14 vaccinees had a rise in jejunal fluid IgA anti-Inaba LPS while 12 (86%) of 14 had rises in jejunal fluid IgA anti-*S.typhi* LPS (p=0.00007, Fisher's exact test, 2-tailed) (Table 8).

2.4 Antibody Secreting Cells Results (PBL Assay)

Cells secreting IgA, IgM, and IgG in response to *S.typhi* and *V.cholerae* were sought 7 days after vaccination (Tables 9 and 10). Cells secreting IgA against *S.typhi* were detected in 13 (93%) of 14 volunteers; cells secreting IgG against *S.typhi* in 9 (64%) of 14 volunteers; and cells secreting IgM against *S.typhi* in 14 (100%) of 14 volunteers (Table 9). Five (36%) of 14 volunteers developed IgA secreting cells; 2 (14%) of 14 had IgG secreting cells; and 6 (43%) of 14 had IgM secreting cells against *V.cholerae* (Table 10).

3. CHALLENGE/PROTECTION RESULTS

Results of the challenge phase are provided in Table 11.

3.1 Controls

| | |
|---|---|
| No. of controls challenged = | 13 |
| No. of cholera cases = | 13 |
| Mean Total Stool Volume = | 2604 ml |
| Mean No. Loose Stools = | 11.6 |
| Mean Incubation Period = | 20.5 hours |
| Mean Peak *V. cholerae* excretion = | $6.2 \times 10^7$ cfu/gram stool |

3.2 Vaccinees

| | |
|---|---|
| No. of vaccinees challenged = | 8 |
| No. of cholera cases = | 6 |
| Mean Total Stool Volume = | 867 ml |
| Mean No. Loose Stools = | 6 |
| Mean Incubation Period = | 25.6 hours |
| Mean Peak *V. cholerae* excretion = | $3.5 \times 10^6$ cfu/gram stool |

4. SUMMARY

The overall protective effect of the vaccine was 25% (6/8 vs 13/13, p=0.13). However, while the protection against all diarrhoeal illness was not significant, the vaccine provided significant protection against total diarrhoeal stool volumes of
a) >1.0 liters (1/8 vs 10/13, p=0.067, 1 tail)
b) >1.5 liters (1/8 vs 9/13, p=0.024, 1 tail)
c) >3.0 liters (0/8 vs 5/13, p=0.06, 1 tail)

The mean stool volume in the controls was 2.6 liters, while it was only 0.87 liters in the vaccinees who had diarrhoea (p=0.01, 2-tailed test). Particularly impressive, in conjunction with the clinical data, are the bacteriological results. The geometric mean peak excretion was $6.2 \times 10^7$ vibrios per gram of stool in the controls versus only $3.5 \times 10^6$ vibrious per gram of stools in the vaccinees. This 10-fold difference is significant (p<0.05, 2-tailed test). Total diarrheal stool volumes in 8 Enterovax typhoid/cholera oral vaccine (EX645) recipients and 13 controls challenged with $1.07 \times 10^6$ pathogenic organisms of *V.cholerae* 01 strain El Tor Inaba N16961.

| Total Diarrhoeal Stool Volume | Vaccines | Controls | p value* |
|---|---|---|---|
| >3.0 liters | 0/8 | 5/13 | 0.06 |
| >2.0 liters | 1/8 | 7/13 | 0.074 |
| >1.0 liters | 1/8 | 10/13 | 0.067 |
| Any diarrhea | 6/8 | 13/13 | |

*Fisher's exact test, one tail

EXAMPLE 6

CONSTRUCTION OF SALMONELLA TYPHI Ty21a STRAINS WITH RFA K-12 AND Vc OAg (INABA) WITH IMPROVED Vc OAg EXPRESSION (EX879 AND EX880)

The challenge trial presented in Example 6, demonstrated that the vaccine strain EX645 provided some limited protection against cholera diarrhoeal disease and significant protection against total diarrhoeal stool volumes and significant reduction in excretion of vibrio organisms.

It was hypothesised that the limited protection offered by this strain was due to the poor ability of EX645 to express the Vc OAg or to express the O-antigen in a form accessible to cells of the immune system. It had been observed that VcOAg expression was strongly inhibited by galactose in the growth medium. The mechanism of such inhibition is not clear but may be due to the LPS cores made in the presence of galactose being unsuitable substrates for VcOAg polymerisation, or the longer Salmonella LPS made under such conditions may "mask" the shorter *V.cholerae* like LPS.

We, therefore, set about to modify the strain EX645 to produce strains which could make demonstrable VcOAg even in the presence of high levels of galactose.

1. STRAIN MODIFICATIONS

Bacteria of strain EX645, grown in Oxoid Nutrient Broth with 0.2% w/v galactose, were spread on Difco Nutrient Agar plates, also with 0.2% w/v galactose (approx $10^8$ bacteria/plate), together with bacteriophage 9NA (about $10^{11}$ plaque forming units/plate, in 0.1 ml NB). The plates were air-dried and incubated for 16 hours at 37° C. Colonies appearing on the plates represented mutants of EX645 which were resistant to the lytic action of the phage. Such colonies appeared at about 1 in $10^6$. Seven such colonies were purified on NA plates, confirmed $9NA^R$, and stored. When grown on galactose-containing plates, all strains were sensitive to phage P221. Strain EX645 is resistant to this phage.

Subsequent examination of two of these strains (called EX879 and EX880) indicated that they still contained plasmid pEVX22, and that V.cholerae-like O-antigen was made by the strains both in the presence and absence of galactose in the growth medium, as demonstrated by hameagglutination inhibition assay analysis (Table 12).

Strain EX880 does not make any Salmonella O-antigen under either condition of growth. The genetic defect in EX880 is not precisely known but may lie either in the rfa gene cluster, which encodes LPS core biosynthetic genes, or in the cluster which encodes Salmonella O-antigen biosynthetic genes.

Strain EX879 is a mutant, as the phage 9NA-resistance may be complemented by a S.typhimurium rfc+ clone, i.e. the strain/plasmid combination is $9NA^s$. Strain EX879 theoretically produces a single *S.typhi*

O-antigen unit attached to the core when the strain is grown with galactose. In practice, full-length Salmonella LPS may also be seen when grown in an excess of galactose (approximately 10 times that required for production of full-length Salmonella LPS in strain EX645). The strain exhibits little masking of the *V.cholerae* O-antigen when compared with EX645.

BACKGROUND

Phage 9NA requires full (long chain) Salmonella LPS as receptor. When EX645 is grown with galactose, such LPS is made. Therefore, mutants resistant to the lytic action of the phage cannot make such LPS.

Phage P221 will not lyse smooth strains of *S. typhi*, but will lyse strains with either 1 or no core-attached O-antigen unit, or with core defects. The 9NA and P221 lysis profiles indicated that strains EX879 and EX880 were incapable of making long-chain Salmonella LPS.

3. CHARACTERISATION OF STRAINS EX879 and EX880

We sought to characterise the strains EX879 and EX880 in relation to strain EX645.
(a) Strains of EX645, EX879 and EX880 are identical in the following characteristics:
appearance,
inability to ferment galactose,
inability to produce $H_2S$,
API 20E Enterobacteriaceae Typing System profile,
auxotrophies,
sensitivity to a variety of antibiotics, and
outer membrane protein profiles on SDS-PAGE.
(b) Strains EX645, EX879 and EX880 all carry the recombinant plasmid as described in Example 4.
(c) The minimal inhibitory concentration (MIC) of tetracycline for EX645, EX879 and EX880 is 4 μg/ml. Using DMC agar supplemented with 15 μg/ml tetracycline, there is low-level reversion (1 in $10^6$) of these strains to high level tetracyclineresistance.

IN VITRO TESTS WITH EX645. EX879 AND EX880

Strain Characterisation (a) Description

When grown in Brain Heart Infusion (BHI) Broth and subsequently examined, all strains are Gram negative rods and motile.

(b) Slide Agglutination Reactions

Organisms grown for 3 passages in BHI broth in the presence (added to the rate of 1 gm/liter) and absence of galactose, gave the following results on slide agglutination.

|  | H:d | Vi | 0:9 | 0:12 | Inaba | Ogawa |
|---|---|---|---|---|---|---|
| Absence of galactose | | | | | | |
| Ty21a | + | − | + | + | − | − |
| EX645 | + | − | + | + | + | − |
| EX879 | + | − | +/− | + | + | − |
| EX880 | + | − | − | − | + | − |
| Presence of galactose | | | | | | |
| Ty21a | + | − | ++ | +++ | − | − |
| EX645 | + | − | ++ | +++ | +/− | − |
| EX879 | + | − | ++ | ++ | +/− | − |
| EX880 | + | − | − | − | +/+ | − |

(c) Ability to ferment galactose

When grown on Galactose Revertant Agar supplemented with 1 g/liter galactose, the vaccine strain ($10^{10}$ organisms) did not produce colonies able to ferment galactose (i.e. galE+ revertants).

|  | 48 hours incubation | 7 days incubation |
|---|---|---|
| Ty21a | no revertants, no lysis | no revertants |
| EX645 | no revertants, no lysis | no revertants |
| EX879 | no revertants, no lysis | no revertants |
| EX880 | no revertants, no lysis | no revertants |

(Galactose Revertant Agar is a minimal (trace amount of Casein) semi-defined medium with galactose as the sole utilisable carbon source.)

(d) Production of $H_2S$

When grown on Kligler iron agar slants none of the strains showed blackening, indicating that no $H_2S$ was produced. This result is confirmed when tested using the API 20E Enterobacteriaceae Typing System.

(e) Biochemical Profile

When tested using the API 20E Enterobacteriaceae Typing System, Ty21a and strains EX645, EX879 and EX880 all yield the same biochemical profile identifying *Salmonella typhi* (Profile 4004500).

(f) Auxotrophies

All strains require L-valine and L-isoleucine to support growth. All strains will grow in a medium consisting of inorganic salts, dextrose and these two amino acids. No other growth requirements have been identified.

(g) Antibiotic sensitivity

Antibiotic sensitivity was assessed by using antibiotic sensitivity test discs placed onto seeded agar plates.

| Antibiotic | Ty21a | EX645 | EX879 | EX880 |
|---|---|---|---|---|
| Ampicillin (2 μg) | S | S | S | S |
| Chloramphenicol (10 μg) | S | S | S | S |
| Kanamycin (30 μg) | S | S | S | S |
| Tetracycline (10 μg) | S | S* | S* | S* |
| Streptomycin (10 μg) | M | R | R | R |
| Rifampicin (2 μg) | R | R | R | R |

S = sensitive
R = resistant
M = moderate resistance
*Although strains are tetracycline sensitive by this measure there is low level reversion to tetracycline resistance.

Galactose - induced Bacteriolysis

When grown in shake flasks in BBL Infusion Broth, supplementation with dextrose-free galactose induced lysis of Ty21a at additions ranging from 1% to 10% galactose by weight. Under the same conditions, EX645, EX879 and EX880 exhibited a retarded rate of growth but did not lyse.

The Plasmid of EX879 and EX880

The plasmid is identical to that in EX645.

The amount of *V.cholerae*-like LPS and *S.typhi* LPS made by strains EX645, EX879 and EX880 under varying growth conditions was quantitated by haemagglutination inhibition (Table 12). Strain EX645 appeared to produce some V. cholerae-like LPS in the absence of galactose, but produced none in the presence of excess galactose. The strain poorly expressed S.typhi LPS in the absence of galactose but appeared to produce some in the presence of excess galactose.

Strain EX879 produced *V.cholerae*-like LPS in the absence of galactose, but no *s.typhi* LPS. In the presence of excess galactose, expression of *V.cholerae*-like LPS decreased and some *S.typhi* LPS was produced.

Strain EX880 produced *V.cholerae*-like LPS but no *S.typhi* LPS irrespective of the amount of galactose added to the growth medium.

NOTE: The results in Table 12 are expressed differently from those in Table 3 due to differences in the assay systems used.

Sensitivity to tetracycline

The MIC of tetracycline for Ty21a was 2 μg/ml, while EX645, EX879 and EX880 had MIC's of 4 μg/ml. When these strains were placed on DMC with tetracycline (15 μg/ml), tetracycline-resistant revertants arose at about 1 in $10^6$.

EXAMPLE 7

IMMUNOGENICITY TRIALS

This example reports on human immunogenicity studies conducted in Adelaide, Australia, using the Enterovax vaccine strain EX880.

Strain EX880 has been tested in human immunogenicity studies in more than 40 healthy adult volunteers. Each volunteer subject received three doses of the vaccine strain EX880, given on days 0, 2 and 5 of the studies. Each dose was taken after an eight hour fast and subjects were then required to fast for a further 45-60 minutes after each dose was given. During the study, venous blood samples were collected prior to the first dose (on day 0) and on days 7 and 14 of the studies.

The vaccine strain was presented as single dose vials containing lyophilised live vaccine organisms which were reconstituted in 10 ml of sterile 0.9% sodium chloride solution. Each dose contained either $3.4\times10^{10}$ or $3.9\times10^{10}$ viable organisms carrying the plasmid, depending on the batch used.

Immune responses were measured using bacteridical serum assays and Enzyme Linked Immunosorbent Assays (ELISA) were carried out on serum to measure the *S.typhi* Ty2 and *V.cholerae* Inaba lipopolysaccharide (LPS) IgA responses.

No significant or severe adverse effects were experienced by any subject, and no volunteer withdrawal was necessary.

A four-fold or greater rise in bactericidal titre was considered to constitute an immune response or seroconversion.

Statistical analysis, using Student's t-test after ln(x) transformation of data, revealed that 67.5% or 27/40 subjects (range 55 to 90%) had a four-fold or greater rise in anti-cholera bactericidal titre.

As expected, no subjects achieved anti-typhi bactericidal seroconversion as measured by anti-S.typhi LPS assays.

EXAMPLE 8

CONSTRUCTION OF A TETRACYCLINE SENSITIVE SALMONELLA TYPHI Ty21a STRAIN WITH RFA K-12 AND Vc OAg (INABA (EX2008)

While the vaccine strains so far constructed were exhibiting significant immunogenicity, the low level reversion to tetracycline resistance was of some concern in the commercial application of the vaccine. Resistance to commonly prescribed antibiotics is generally considered by regulatory authorities to be unacceptable for commercial use.

In order to remove the residual reversion to tetracycline resistance, strain EX879 was modified as follows:

Plasmid pEVX22 (from EX521) was partially digested with removing approximately 3.5 kb of DNA including most of the tetracycline resistance genes. The new plasmid, called pEVX59 (FIG. 21) was transformed into strain EX100. The resultant strain was called EX843 and was shown to be tetracycline sensitive.

Plasmid pEVX59 was then transformed into strain EX2001 with selection for thymine independent growth. A resultant strain was called EX2006. Strain EX2001 is a *Salmonella typhimurium* LT2 galE mutant selected thyA and cured of its virulence plasmid.

Strain EX879 was cured of plasmid pEVX22 by passage on medium containing thymine and a resistant thyA strain was selected and called EX956. Plasmid pEVX59 (from EX2006) was transformed into EX956 with selection for $thyA^+$ on CBT plates. One such transformed strain was called EX2008.

Strain EX2008 carried the $tet^s$ plasmid pEVX59. The strain has been screened $rif^R$ and shown to express Vc OAg by slide agglutination, haemagglutination inhibition assay and SDS-PAGE gel.

In vitro tests with EX2008

(a) Strain EX2008 was identical to strains EX645, EX879 and EX880 in the following characteristics:

appearance
inability to ferment galactose
inability to produce $H_2S$, and
API 20E Enterobacteriaceae Typing System Profile.

All testing was conducted as described in Examples 4 and 6.

(b) Antibiotic Sensitivity

Strain EX2008 exhibited similar sensitivity to that shown by strains EX645, EX879 and EX880, to the following antibiotics: ampicillin (2 μg), chloramphenicol (10 μg), Kanamycin (30 μg), streptomycin (10 μg) and rifampicin (2 μg) using antibiotic sensitivity test discs placed onto seeded agar plates.

(c) Sensitivity to tetracycline

Strain EX2008 showed similar sensitivity to tetracycline (10 μg) as Ty21a when assessed using antibiotic sensitivity test discs placed onto seeded agar plates. The MIC of tetracycline for Ty21a and EX2008 was 2 μg/ml, while EX645, EX879 and EX880 had MIC's of 4 μg/ml. When strain EX2008 was plated on DMC

EXAMPLE 9

CONSTRUCTION OF A TETRACYCLINE SENSITIVE SALMONELLA TYPHI Ty21a STRAIN WITH RFA K-12 AND Vc OAo (INABA) (EX2007)

$(1 \times 10^8)$ with tetracycline 15 μg/ml, no tetracycline-resistant revertants arose.

Figure 21:
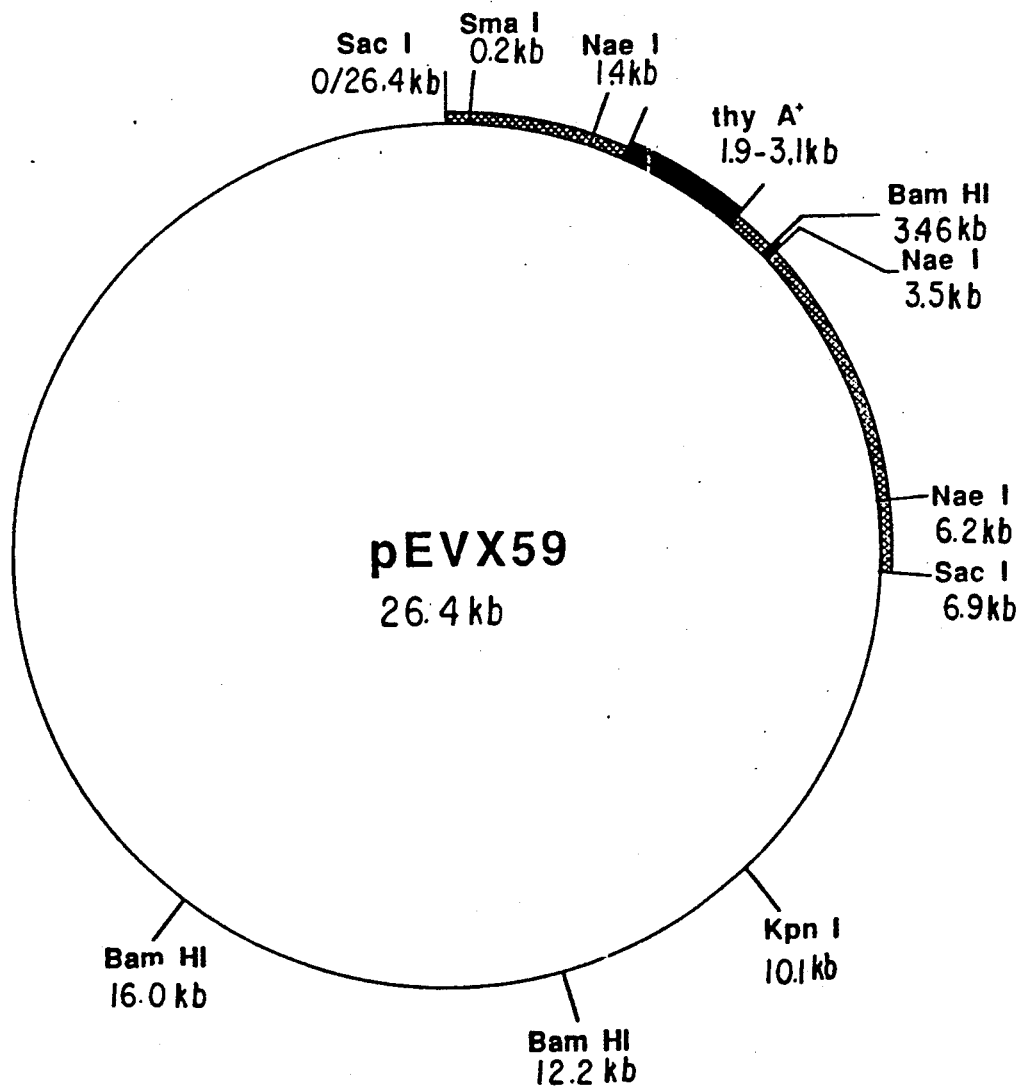

In order to remove the residual reversion to tetracycline resistance of strain EX880, the strain was modified as follows:

Plasmid pEVX22 (from EX 521) was partially digested with NaeI, removing approximately 3.5 kb of DNA including most of the tetracycline resistance genes. The new plasmid, called pEVX59 (FIG. 21) was transformed into strain EX100. The resultant strain was called EX843 and was shown to be tetracycline sensitive.

Plasmid PEVX59 was then transformed into strain EX2001 with selection for thymine independent growth. A resultant strain was called EX2006. Strain EX2001 is a *Salmonella typhimurium* LT2 calE mutant selected thyA and curred of its virulence plasmid.

Strain EX880 was cured of plasmid pEVX22 by passage on medium containing thymine and a resistant thyA strain was selected and called EX931. Plasmid pEVX59 (from EX2006) was transformed into EX931 with selection for thyA+ on CBT plates. One such transformed strain was called EX2007.

Strain EX2007 carried the tet$^S$ plasmid pEVX59. The strain has been screened rif$^R$ and shown to express Vc OAg by slide agglutination, haemagglutination inhibition assay and SDS-PAGE gel.

TABLE 1

The strains used in the construction of vaccine strains in this specification.

| Strain | Genotype | Source/Description/Derivation |
|---|---|---|
| S. TYPHI STRAINS | | |
| Ty2 | cys⁻, trp⁻ | Institute of Medical and Veterinary Science, Adelaide |
| EX543 | Ty2, via | D. Hone |
| Ty21a | galE, via (Vi⁻), ilv | R. Germanier |
| E759 | Ty21a rpoB | Rifampin-resistant derivative of Ty21a |
| V487 | E759 (pPM1004) | E759 with plasmid pPM1004, by conjugation; Tc$^R$ |
| EX210 | V487 (rfa, mtl-16::Tn9)$^{K-12}$ | V487 with the rfa region of *E. coli* K-12, mtl⁻, Cm$^R$ |
| EX233 | E759 (rfa, mtl-16::Tn9)$^{K-12}$ | Spontaneous Tc$^S$ derivative of EX210; pPM1004 lost |
| EX256 | E759 (rfa, mtl+)$^{K-12}$ | mtl+ revertant of EX233, Cm$^S$ (Tn9 precise excision) |
| EX259 | EX256 thyA⁻ | By selection on thymine/trimethoprim |
| EX535 | EX259 (pEVX22) | Vaccine strain first isolate. From EX259 by conjugation. |
| EX645 | EX259 (pEVX22) | Vaccine strain, re-isolate |
| EX363 | EX259 (pEVX14)* | From EX320 × EX259 cross, selecting thy+ deoxycholate-resistance |
| EX956 | EX879 (pEVX22)⁻ | EX879 cured of plasmid pEVX22 by passage on thymine |
| EX2008 | EX956 (pEVX59) | EX956 with plasmid pEVX59 by transformation selecting thyA+. |
| EX880 | EX645 rfb on rfa | Screened rif$^R$, Vc OAg+ Phage 9NA-resistant derivative of EX645. Does not produce typhi O-antigen |
| EX879 | EX645 rfc | Phage 9NA-resistant derivative of EX645. Produces a typhi LPS with altered O-antigen chain length when grown without excess galactose. |
| EX2007 | EX931 (pEVX59) | EVX931 with plasmid pEVX59 by transformation, selecting thyA+, screened rif$^R$, VcOAg+ |
| EX931 | EX259 rfb | EX880 without pEVX22, thyA⁻ |
| E. COLI K-12 STRAINS | | |
| PK3 | Hfr P0131, thr-1, thi-1, leuB6, lacY1, azi-15, tonA21, supE44, lambda⁻ | B. Bachmann |
| NK6701 | IN (rrnD-rrnE)1, mtl-16::Tn9, lambda⁻ | B. Bachmann |
| EX170 | PK3 mtl-16 Tn9 | By transduction from NK6701 |
| P400 | thr-1, leu-6, proA2, lacY1, supE44, galK2, non-9, rpsL31 xyl-5, mtl-1, argE3, thi-1, ara-14, F⁻, lambda⁻ | P. Reeves |
| LE392 | supF, supE, hsdR, galK, trpR, metB, lacY, F⁻ | B. Bachmann |
| EX98 | LE392 thyA⁻ | By selection on thymine/trimethoprim |
| EX691 | LE392 thyA⁻ | By selection on thymine/trimethoprim |
| KL96 | relA1, thi-1, HfrPO44 lambda⁻ | B. Bachmann |
| V484 | KL96 (pPM1004) | By transformation, selecting Tc$^R$ |
| EX239 | KL96 thyA⁻ | By selection on thymine/trimethoprim |
| P2495 | thr-1, leu-6, proA2, lacY1, galK2, trp (UAG), his-4, non-9, tolC210::Tn10-48, rpsL31, xyl-5, mtl-1, argE3, F⁻, lambda⁻ | P. Reeves |
| EX252 | EX239 tolC210::Tn10-48 | By transduction from P2495, selecting Tc$^R$ |
| EX484 | EX252 (pEVX22) | By transformation, selecting thymine prototrophy |
| DH1 | gyrA96, recA1, relA1, end-A, thi-1, hsdR17, supE44, lambda⁻ | B. Bachmann |
| 525/4 | *E. coli* 071 LT+ | Institute of Medical & Veterinary Science, Adelaide |
| KL228 | thi, leu lacY, gal supE Hfr P074 | B. Bachmann |
| EX173 | KL228 mtl::Tn9 | By P1vir transduction from NK6701 |
| EX260 | EX170 tolC210::Tn10 | By transduction from P2495, selecting Tc$^R$ |
| EX320 | EX252 (pEVX14) | By transformation, with selection on minimal medium |
| EX178 | V484 thyA⁻ | By trimethoprim selection |
| E381 | *E. coli* K-12 recA | P. Manning |
| EX100 | E381 thyA | By selection on trimethoprim/thymine |

TABLE 1-continued

The strains used in the construction of vaccine strains in this specification.

| Strain | Genotype | Source/Description/Derivation |
|---|---|---|
| EX843 | EX100 (pEVX59) | EX100 with plasmid pEVX59 by transformation |
| EX521 | EX100 (pEVX22) | EX100 with plasmid pEVX22 by transformation |
| *S. TYPHIMURIUM* STRAINS | | |
| G30 | galE | This laboratory |
| EX262 | G30 (rfa, mtl-16::Tn9)$^{K-12}$ | |
| SGSC262 | trp, metA, metE, ilv, xyl, hsdL, hsdS, rpsL, rfaG 3037 | B. Stocker |
| EX225 | SGSC262, ilv$^+$, xyl$^+$ (rfa, mtl-16::Tn9)$^{K-12}$ | By mating with EX170 |
| V490 | G30 rpsL (pPM1004) | By transformation, selecting Tc$^R$ |
| EX200 | LB5010 (met+, ilv+, rfa, mtl-16::Tn9)$^{K-12}$ | Cross EX170x *S. typhimurium* strain LB5010 selecting str$^R$ and cml$^R$ |
| EX361 | EX200 thyA | By trimethoprim selection |
| EX216 | EX200 (pPM1004) | By crossing EX200 with EX178, selecting Rc$^R$, thy$^+$ |
| E246 | *S. typhimurium* LT2 galE, restriciton$^-$, modification$^+$ | L. Bullas |
| EX143 | E246 thyA | By selection on thymine/trimethoprim |
| EX2001 | EX143 vir$^-$ | EX143 cured of its virulence plasmid |
| EX2006 | EX2001 (pEVX59) | EX2001 with plasmid pEVX59 by transformation and selection for thyA$^+$ |
| EX206 | (rfa mtl::tn9)$^{K-12}$ | V490 conjugated with EX173 screened VcOAg+, selecting cml$^r$, str$^R$, tet$^R$ |

TABLE 2

Activities of the enzymes encoded by the galE, galT and galK genes in various strains.

| Strain | galE | galT | galK |
|---|---|---|---|
| EX542 (Ty2) | 17.6 | 10.2 | 18.3 |
| Ty21a | ND | 0.738 | 2.29 |
| EX645 | ND | 0.650 | 3.79 |

Enzyme units are micromoles of substrate converted per mg protein, per h.
ND = no detectable activity

TABLE 3

Haemagglutination inhibition assay of EX645 and Ty21a for LPS expression when grown with varying galactose levels

| Grown in the absence of galactose | | |
|---|---|---|
| | *S. typhi* Ty2Vi$^-$ | *V. cholerae* Inaba 569B |
| Ty21a | <0.8% | <1.6% |
| EX645 | <0.8% | 25-50% |
| Grown in the presence of excess galactose | | |
| | Ty2Vi$^-$ | 569B |
| Ty21a | 50% | <1.6% |
| EX645 | 50% | <1.6% |
| Grown in the presence of limiting galactose | | |
| | Ty2Vi$^-$ | 569B |
| Ty21a | 25-50% | <1.6% |

TABLE 3-continued

Haemagglutination inhibition assay of EX645 and Ty21a for LPS expression when grown with varying galactose levels

| EX645 | 6.25-12.5% | 25-50% |
|---|---|---|

Percentages quoted are comparison with the cell type native for that LPS type in the same assay.
Limits of detection:
*S. typhi* Ty2Vi$^-$ 0.8%
*V. cholerae* Inaba 1.6%

TABLE 4

Numbers of restriction enzyme sites seen on digestion of various plasmids with various enzymes

| | Plasmid | | |
|---|---|---|---|
| Enzyme(s) | pEVX22 | pEVX5 | pBTAH |
| SacI | 2 | 1 | NS |
| BamHI | 3 | 1 | NS |
| SacI and BamHI | 5 | 2 | NS |
| HindIII | 10 | 2 | 2 |
| SmaI | 1 | 1 | — |
| HpaI | 1 | 1 | — |
| EcoRI | 7 | 1 | — |
| EcoRI and SacI | 9 | 2 | — |
| KpnI | 1 | NS | — |
| KpnI and SmaI | 2 | 1 | — |
| SmaI and PstI | 3 | 2 | — |

NS = no site
— = not done

TABLE 5

Serum vibriocidal (Inaba) responses after vaccination with EVAX CTV (EX645) vaccine - Center for Vaccine Development Analysis

| | Vibriocidal Response* | | |
|---|---|---|---|
| | Pre | 14 Days | Seroconversion+ |
| CHALLENGED VOLUNTEERS | | | |
| 11001-4 | 20 | 20 | — |
| 11001-5 | <20 | <20 | — |
| 11001-9 | <20 | <20 | — |
| 11001-10 | 20 | 40 | — |
| 11001-12 | <20 | 80 | + |
| 11001-13 | 40 | 320 | + |
| 11001-14 | 40 | 80 | — |
| 11001-17 | 80 | 40 | — |
| Geometric Mean Titer | 21.8 | 40.0 | |
| VOLUNTEERS NOT CHALLENGED | | | |
| 11001-1 | <20 | 40 | + |
| 11001-3 | <20 | 40 | + |
| 11001-6 | 2560 | 2560 | — |
| 11001-15 | <20 | 160 | + |
| 11001-16 | 20 | 20 | — |
| 11001-18 | <20 | <20 | — |
| Geometric Mean Titer | 28.3 | 71.3 | |
| Percent Seroconversion | | | 36% |

*Expressed as reciprocal titer
+Seroconversion defined as a 4-fold rise in titer

TABLE 6

Serum vibriocidal (Inaba) responses after vaccination with EVAC CTV (EX645) vaccine - Enterovax Limited Analysis

| | Vibriocidal Response* | | |
|---|---|---|---|
| | Pre | 14 Days | Seroconversion+ |
| CHALLENGED VOLUNTEERS | | | |
| 11001-4 | 9 | 13 | — |
| 11001-5 | 5 | 7 | — |
| 11001-9 | <5 | <5 | — |
| 11001-10 | 58 | 280 | + |
| 11001-12 | <5 | 320 | + |
| 11001-13 | 100 | 1600 | + |
| 11001-14 | 190 | 230 | — |
| 11001-17 | 330 | 210 | — |
| Geometric Mean Titer | 23.8 | 79.4 | |
| Geometric | | | 3.0 |

TABLE 6-continued

Serum vibriocidal (Inaba) responses after vaccination with EVAC CTV (EX645) vaccine - Enterovax Limited Analysis

| | Vibriocidal Response* | | |
|---|---|---|---|
| | Pre | 14 Days | Seroconversion+ |
| Mean Fold Rise | | | |
| VOLUNTEERS NOT CHALLENGED | | | |
| 11001-1 | 13 | 74 | + |
| 11001-3 | 20 | 510 | + |
| 11001-6 | 90,000 | 82,000 | − |
| 11001-15 | 5 | 940 | + |
| 11001-16 | 14 | 50 | − |
| 11001-18 | <5 | <5 | − |
| Geometric Mean Titer | 40.0 | 267 | |
| Geometric Mean Fold Rise | | 6.7 | |
| Percent Seroconversion | | | 43% |

*Expressed as reciprocal titer
+Seroconversion defined as a 4-fold rise in titer

TABLE 7

Serum antibodies against LPS O-antigen after vaccination with strain EX645

| | ANTI-LPS RESPONSE* | | | | | | | |
|---|---|---|---|---|---|---|---|---|
| | INABA | | | | S. TYPHI | | | |
| | IgG | | IgA | | IgG** | | IgA | |
| | Pre | Peak | Pre | Peak | Pre | Peak | Pre | Peak |
| CHALLENGED VOLUNTEERS | | | | | | | | |
| 11001-4 | 320 | 160 | 160 | 320 | 0.51 | 2.69++ | 40 | 2560+ |
| 11001-5 | 40 | 40 | <40 | <40 | 0.26 | 0.75++ | 40 | 160+ |
| 11001-9 | <40 | 40 | <40 | <40 | 1.25 | 2.02++ | 40 | 80 |
| 11001-10 | 40 | 40 | <40 | <40 | 0.27 | 1.11++ | 160 | 640+ |
| 11001-12 | <40 | 40 | 40 | 40 | 0.15 | 0.77++ | 20 | 320+ |
| 11001-13 | 80 | 80 | <40 | 80+ | 0.25 | 2.10++ | 20 | 160+ |
| 11001-14 | 2560 | 2560 | <40 | <40 | 0.56 | 0.99++ | 80 | 320+ |
| 11001-17 | 40 | 40 | <40 | 40 | 0.18 | 1.39++ | 40 | 40 |
| VOLUNTEERS NOT CHALLENGED | | | | | | | | |
| 11001-1 | 160 | 320 | <40 | <40 | 0.22 | 1.03++ | <20 | 40+ |
| 11001-3 | 40 | 80 | <40 | <40 | 0.33 | 1.93++ | 20 | 320+ |
| 11001-6 | 80 | 160 | 40 | 40 | 0.31 | 1.01++ | 160 | 320 |
| 11001-15 | 40 | 40 | <40 | <40 | 0.29 | 1.02++ | 40 | 320+ |
| 11001-16 | 40 | 40 | <40 | <40 | 0.05 | 0.31++ | 20 | 40 |
| 11001-18 | <40 | 80+ | 40 | 40 | 0.27 | 0.47++ | 40 | 640+ |
| Percent Seroconversion | | 7% | | 7% | | 100% | | 77% |

*Expressed as reciprocal titer
**Expressed as net O.D. at 405 nm
+Significant seroconversion, defined as a 4-fold rise in titer
++Significant seroconversion, defined as a net O.D. ≧0.15

TABLE 8

Jejunal fluid IgA antibodies against LPS O-antigen after vaccination with cholera/typhoid strain EX645

| | IgA Anti-LPS Response* | | | |
|---|---|---|---|---|
| | Inaba | | S. typhi | |
| | Pre | Peak | Pre | Peak |
| CHALLENGED VOLUNTEERS | | | | |
| 11001-4 | 8 | 8 | 16 | >128+ |
| 11001-5 | <4 | <4 | 4 | 64+ |
| 11001-9 | <4 | <4 | 4 | 128+ |
| 11001-10 | <4 | <4 | 4 | 1.28+ |
| 11001-12 | <4 | <4 | <4 | 32+ |
| 11001-13 | <4 | <4 | 4 | 256+ |
| 11001-14 | <4 | <4 | 4 | 32+ |
| 11001-17 | <4 | <4 | 8 | 64+ |
| VOLUNTEERS NOT CHALLENGED | | | | |
| 11001-1 | <4 | <4 | 4 | 16+ |
| 11001-3 | 4 | <4 | 16 | 128+ |
| 11001-6 | <4 | <4 | 4 | 32+ |
| 11001-15 | 8 | <4 | <4 | 64+ |
| 11001-16 | <4 | 8+ | 8 | 16 |
| 11001-18 | <4 | <4 | 16 | 32 |
| Percent Seroconversion | | 7% | | 86% |

Jejunal fluids were collected before and days 7 and 14 after ingestion of the first dose of vaccine.
*Expressed as reciprocal titer
+Significant immunoconversion defined as a 4-fold rise in titer

TABLE 9

Antibody secreting cells after vaccination with cholera/typhoid vaccine strain EX645: Response to S. typhi Ty2 (PLB Assay)

| | IgA | | IgG | | IgM | |
|---|---|---|---|---|---|---|
| | Day 0 | Day 7 | Day 0 | Day 7 | Day 0 | Day 7 |
| CHALLENGED VOLUNTEERS | | | | | | |
| 11001-4 | 0.03 | >2.00+ | 0.03 | 1.60+ | 0.07 | 0.21+ |
| 11001-5 | 0.02 | 1.86+ | 0.04 | 0.21+ | 0.05 | 1.01+ |
| 11001-9 | 0.00 | 0.20+ | 0.02 | 0.12+ | 0.08 | 0.27+ |
| 11001-10 | 0.01 | >2.00+ | 0.03 | 0.20+ | 0.02 | 0.24+ |
| 11001-12 | 0.05 | 1.91+ | 0.01 | 0.29+ | 0.05 | 0.42+ |
| 11001-13 | 0.00 | 0.32+ | 0.01 | 0.37+ | 0.05 | 0.36+ |
| 11001-14 | 0.03 | 0.85+ | 0.03 | 0.07 | 0.09 | 0.47+ |
| 11001-17 | 0.01 | 0.41+ | 0.01 | 0.14+ | 0.08 | 0.68+ |
| VOLUNTEERS NOT CHALLENGED | | | | | | |
| 11001-1 | 0.03 | 0.32+ | 0.01 | 0.30+ | 0.04 | 0.13+ |
| 11001-3 | 0.02 | 0.32+ | 0.00 | 0.23+ | 0.05 | 0.43+ |
| 11001-6 | 0.00 | 1.16+ | 0.01 | 0.05 | 0.04 | 0.84+ |
| 11001-15 | 0.05 | 1.66+ | 0.02 | 0.09 | 0.10 | 0.30+ |
| 11001-16 | 0.00 | 0.17+ | 0.00 | 0.01 | 0.01 | 0.37+ |
| 11001-18 | 0.01 | 0.04 | 0.06 | 0.00 | 0.09 | 0.16+ |
| Percent Conversion | | 93% | | 64% | | 100% |

+Significance IgA, IgG and IgM responses defined as a post-vaccination O.D. ≧0.10 absorbance units

TABLE 10

Antibody secreting cells after vaccination with cholera/typhoid vaccine strain EX645: Response to V. cholerae 569B (PBL assay)

| | IgA | | IgG | | IgM | |
|---|---|---|---|---|---|---|
| | Day 0 | Day 7 | Day 0 | Day 7 | Day 0 | Day 7 |
| CHALLENGED VOLUNTEERS | | | | | | |
| 11001-4 | 0.05 | 0.08+ | 0.00 | 0.00 | 0.00 | 0.16+ |
| 11001-5 | 0.02 | 0.06+ | 0.02 | 0.01 | 0.06 | 0.09+ |
| 11001-9 | 0.01 | 0.00 | 0.00 | 0.07+ | 0.04 | 0.10+ |
| 11001-10 | 0.04 | 0.17+ | 0.00 | 0.00 | 0.07 | 0.17+ |
| 11001-12 | 0.00 | 0.05 | 0.00 | 0.06+ | 0.07 | 0.08 |
| 11001-13 | 0.01 | 0.08+ | 0.00 | 0.00 | 0.03 | 0.04 |
| 11001-14 | 0.02 | 0.02 | 0.00 | 0.00 | 0.08 | 0.08 |
| 11001-17 | 0.00 | 0.03 | 0.00 | 0.00 | 0.07 | 0.09+ |
| VOLUNTEERS NOT CHALLENGED | | | | | | |
| 11001-1 | 0.05 | 0.01 | 0.00 | 0.00 | 0.05 | 0.02 |
| 11001-3 | 0.00 | 0.00 | 0.02 | 0.00 | 0.05 | 0.08 |
| 11001-6 | 0.07 | 0.09+ | 0.01 | 0.00 | 0.10 | 0.07 |
| 11001-15 | 0.04 | 0.04 | 0.00 | 0.00 | 0.09 | 0.12+ |
| 11001-16 | 0.02 | 0.03 | 0.00 | 0.00 | 0.03 | 0.03 |
| 11001-18 | 0.10 | 0.00 | 0.00 | 0.00 | 0.10 | 0.06 |
| Percent Conversion | | 36% | | 14% | | 43% |

+IgA response is defined as a post-vaccination O.D. ≧0.06 absorbance units.
IgG response is defined as a post-vaccination O.D. ≧0.01 absorbance units.
IgM response is defined as a post-vaccination O.D. ≧0.09 absorbance units.

TABLE 11

Results of challenge phase of cholera CVD 11000 study

| CVD NO. | TOTAL STOOL VOLUME | NO. LOOSE STOOLS | INCUBATION PERIOD | PEAK V. CHOLERAE EXCRETION |
|---|---|---|---|---|
| CONTROLS | | | | |
| 11002-1 | 2054 ml | 10 | 31.5 hr. | $1.2 \times 10^8$ organisms/gm |
| 11002-2 | 1168 | 8 | 22.0 | $1.0 \times 10^8$ |
| 11002-3 | 889 | 8 | 22.0 | $7.5 \times 10^7$ |
| 11002-6 | 4399 | 17 | 16.5 | $1.5 \times 10^8$ |
| 11002-9 | 1819 | 13 | 13.5 | $3.0 \times 10^8$ |
| 11002-12 | 1597 + incont. | 6 | 16.0 | $5.0 \times 10^6$ |
| 11002-15 | 4619 | 12 | 17.5 | $8.0 \times 10^6$ |
| 11002-17 | 3405 | 11 | 21.0 | $1.0 \times 10^8$ |
| 11002-19 | 906 | 8 | 32.0 | $1.0 \times 10^8$ |
| 11002-20 | 622 | 3 | 27.5 | $1.0 \times 10^7$ |
| 11002-21 | 3294 | 20 | 22.0 | $1.0 \times 10^8$ |
| 11002-22 | 2634 | 13 | 5.5 | $1.0 \times 10^8$ |
| 11002-23 | 6434 | 22 | 20.0 | $1.3 \times 10^8$ |
| MEAN | 2604* | 11.6 | 20.5 | $6.2 \times 10^{7+}$ |
| VACCINEES | | | | |
| 11002-4 | 956 | 7 | 17.0 | $1.0 \times 10^8$ |
| 11002-5 | 497 | 2 | 25.5 | $1.5 \times 10^7$ |
| 11002-7 | 2053 | 9 | 20.0 | $7.5 \times 10^7$ |
| 11002-8 | 784 | 7 | 53.0 | $6.5 \times 10^5$ |
| 11002-10 | (—) | (0) | (—) | $(2.0 \times 10^4)$ |
| 11002-11 | (—) | (0) | (—) | $(2.7 \times 10^3)$ |
| 11002-14 | 312 | 5 | 16.0 | $1.1 \times 10^8$ |
| 11002-16 | 602 | 6 | 22.0 | $5.0 \times 10^7$ |
| MEAN | *867 | 6 | 25.6 | $3.5 \times 10^{6+}$ |

*$p < 0.05$, comparing total stool volumes of controls and vaccinees
+$p < 0.05$, comparing peak *V. cholerae* excretion of controls and vaccinees
( ) negative against standard disease criteria

TABLE 12

Haemagglutination inhibition assay of EX645, EX879 and EX880 for LPS expression when grown with varying galactose levels.

| Grown in absence of galactose | | |
|---|---|---|
| | S. typhi Ty2Vi⁻ | V. cholerae 569B Inaba |
| EX645 | 0.4% | 12.5% |
| EX879 | <0.4% | 25% |
| EX880 | <0.4% | 25% |

| Grown in presence of limiting galactose (0.0001% w/v) | | |
|---|---|---|
| | Ty2 Vi⁻ | Inaba |
| EX645 | 1.6% | 12.5% |
| EX879 | 0.8% | 25% |
| EX880 | <0.4% | 25% |

| Grown in presence of excess galactose (0.1% w/v) | | |
|---|---|---|
| | Ty2 Vi⁻ | Inaba |
| EX645 | 6.2% | <0.2% |
| EX879 | 3.1% | 3.1% |
| EX880 | <0.4% | 25% |

Limits of detection:
S. typhi  Ty2 Vi⁻ 0.4%
V. cholerae  Inaba 0.2%

Finally, it is to be understood that various other modifications and/or alterations may be made without departing from the spirit of the present invention as outlined herein.

We claim:

1. A vaccine composition comprising an avirulent Salmonella - *Escherichia coli* hybrid strain, wherein said hybrid strain is made by modifying an avirulent strain of Salmonella so that the lipopolysaccharide core region produced by the hybrid is the *E. coli* lipopolysaccharide core region and the hybrid further produces a *Vibrio cholerae* O-antigen.

2. The vaccine composition of claim 1 wherein the Salmonella strain is a *Salmonella typhimurium* strain.

3. The vaccine composition of claim 1 wherein the Salmonella strain is a *Salmonella typhi* strain.

4. The vaccine composition of claim 3 wherein the hybrid strain is selected from the group consisting of EX645, EX880, EX2007 or a variant or mutant thereof which produces an E. coli lipopolysaccharide core region and a *vibrio cholerae* O-antigen.

5. The vaccine composition of claim 1 wherein the hybrid strain is resistant to the lytic action of phage 9NA when grown in a nutrient medium containing 0.2% w/v galactose.

6. The vaccine composition of claim 5 wherein the Salmonella strain is a *Salmonella typhi* strain.

7. The vaccine composition of claim 5, in which the hybrid strain is a non-reverting tetracycline-sensitive mutant.

8. The vaccine composition of claim 1, wherein the hybrid strain is derived by introducing into the Salmonella strain the rfa locus lacated at approximately 81 minutes on the *E. coli* K-12 genetic map.

9. The vaccine composition of claim 1 wherein the Salmonella strain is thyA⁻ and the hybrid strain is thyA⁺.

10. The vaccine composition of claim 9 wherein the Salmonella strain is a *Salmonella typhi* strain.

11. A method for the immunization of a mammal against an enteric disease comprising administering to the mammal an immunizing amount of a vaccine composition according to claim 1.

12. A method for the immunization of a mammal against cholera which comprises administering to the mammal an immunizing amount of a vaccine composition according to claim 1.

13. The method of claim 12 wherein the Salmonella strain is a *Salmonella typhi* strain.

14. A vaccine composition comprising an avirulent Salmonella-*E. coli* hybrid strain, wherein said hybrid strain is made by insertion of the following genes into a thyA- avirulent parental strain of *Salmonella typhi*:

(a) at last a portion of the rfa locus located at approximately 81 min on the E. coli K-12 genetic map, said portion comprising genes encoding the enzymes required to form the core region of the E. coli lipopolysaccharide, wherein said inserted portion replaces the corresponding parental Salmonella genes;

(b) genes encoding the expression of a *Vibrio cholerae* O-antigen, and (c) a non-antibiotic marker.

15. The vaccine composition of claim 14 in which the non-antibiotic marker is thyA and the parental Salmonella strain is thyA-.

16. A method for the immunization of a mammal against an enteric disease comprising administering to the mammal an immunizing amount of a vaccine composition according to claim 15.

* * * * *